US006517837B1

(12) United States Patent
Scanlan et al.

(10) Patent No.: US 6,517,837 B1
(45) Date of Patent: Feb. 11, 2003

(54) ISOLATED NUCLEIC ACID MOLECULES ASSOCIATED WITH COLON CANCER AND METHODS FOR DIAGNOSING AND TREATING COLON CANCER

(76) Inventors: Matthew J. Scanlan, 1275 York Ave., New York, NY (US) 10021; Yao-Tseng Chen, 525 E. 68th St., New York, NY (US) 10021; Elisabeth Stockert, 1275 York Ave., New York, NY (US) 10021; Lloyd J. Old, 1345 Avenue of the Americas, New York, NY (US) 10105

( * ) Notice: Subject to any disclaimer, the term of this patent is extended or adjusted under 35 U.S.C. 154(b) by 0 days.

(21) Appl. No.: 09/510,543

(22) Filed: Feb. 22, 2000

Related U.S. Application Data

(60) Division of application No. 09/102,322, filed on Jun. 22, 1998, now Pat. No. 6,403,373, which is a continuation-in-part of application No. 08/948,705, filed on Oct. 10, 1997, now Pat. No. 6,043,084.

(51) Int. Cl.[7] .................. A61K 39/00; A61K 39/38; A61K 39/29; C07K 1/00; C07K 14/00; C07K 17/00; C07H 21/02; C07H 21/04
(52) U.S. Cl. .................. 424/184.1; 424/227.1; 530/350; 536/23.1
(58) Field of Search .......... 424/277.1, 184.1; 530/350; 536/23.1

(56) References Cited

U.S. PATENT DOCUMENTS 5,470,730 A * 11/1995 Greenberg et al.
5,698,396 A  12/1997 Pfreundschuh

OTHER PUBLICATIONS

Sahin et al., Proc. Natl. Acad. Sci., vol. 92, pp. 11810–11813, Dec. 1995.*
Alberts, et al. (Molecular Biology of the Cell, 3rd edition, 1994.*
Chen et al., *Proc. Natl. Acad. Sci. USA* 94: 1914–1918 (1997).
de Plaen et al., *Proc. Natl. Sci. USA* 85:2275, 1988.
Mandelboim et al., *Nature* 369:69 1994.
van der Bruggen et al., *Science* 254:1643–1647, 1991.
Brichard et al., *J. Exp. Med.* 178:489–495, 1993.
Coulie et al., *J. Exp. Med.* 180:35–42, 1994.
Kawakami et al., *Proc. Natl. Acad. Sci. USA* 91:3515–3519, 1994.
Oettgen et al., *Immunol. Allerg. Clin. North. Am.* 10:607–637, 1990.
Sahin et al., *Proc. Natl. Acad. Sci. USA* 92:11810–11913, 1995.
Crew et al., *EMBO J* 144:2333–2340, 1995.
Van Amsterdam, J., Database search of public nucleic acids databases using BLAST algorithm, http://www.ncbi.nlm.nih.gov/blast.cgi, Jul. 13, 1998.

* cited by examiner

*Primary Examiner*—Sheela Huff
*Assistant Examiner*—Natalie Davis

(57) ABSTRACT

Various molecules associated with disorders such as cancer are disclosed. The invention also discloses diagnostic and therapeutic methods based upon these molecules, as well as compositions for stimulating an immune response and methods for identifying cancer-associated nucleic acid and polypeptide molecules.

28 Claims, No Drawings

ISOLATED NUCLEIC ACID MOLECULES ASSOCIATED WITH COLON CANCER AND METHODS FOR DIAGNOSING AND TREATING COLON CANCER

RELATED APPLICATION

This application is a divisional of U.S. application Ser. No. 09/102,322, filed Jun. 22, 1998, now U.S. Pat. No. 6,403,373, which is a continuation-in-part of U.S. application Ser. No. 08/948,705, filed on Oct. 10, 1997, now U.S. Pat. No. 6,043,084, both of which are incorporated by reference herein.

FIELD OF THE INVENTION

This invention relates to the isolation of genes associated with renal and/or colon cancer, methods of diagnosing renal and/or colon cancer using these, and the use of other known genes in diagnosis of, as well as therapeutic approaches to treating such conditions.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., *Proc. Acad. Natl. Sci. USA* 85: 2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by anti-tumor cytolytic T cell clones. The biochemical approach, exemplified by, e.g., Mandelboim, et al., *Nature* 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytolytic T-lymphocytes ("CTLs"). These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of CTLs with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., *Science* 254: 1643–1647 (1991); Brichard et al., *J. Exp. Med.* 178: 489–495 (1993); Coulie, et al., *J. Exp. Med.* 180: 35–42 (1994); Kawakami, et al., *Proc. Natl. Acad Sci. USA* 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., *Immunol. Allerg. Clin. North. Am.* 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., *Proc. Natl. Acad. Sci. USA* 92: 11810–11913 (1995), incorporated by reference. Also, see U.S. Pat. No. 5,698,396. Both of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., *EMBO J.* 144: 2333–2340 (1995).

The SEREX methodology has now been applied to various tumors, including colon and renal cancer samples. Several nucleic acid molecules have been newly isolated and sequenced, and are now associated with stomach cancer. Further, a pattern of expression involving these, as well as previously isolated genes has been found to be associated with renal and colon cancer. These results are the subject of this application, which is elaborated upon in the disclosure which follows.

DETAILED DESCRIPTION OF PREFERRED EMBODIMENTS

EXAMPLE 1

Tumor samples were obtained as surgical samples, and were frozen at −80 C. until ready for use.

Total RNA was then isolated from the samples, using the well known guanidium thiocyanate method of Chirgwin, et al., *Biochemistry* 18: 5294–5299 (1979), incorporated by reference. The thus obtained total RNA was then purified to isolate all poly A$^+$ RNA, using commercially available products designed for this purpose.

The poly A+ RNA was then converted into cDNA, and ligated into λZAP, a well known expression vector.

Three cDNA libraries were constructed in this way, using colorectal carcinoma samples. A fourth library, also from colorectal carcinoma, was prepared, albeit in a different way. The reasons for this difference will be clear in the examples, infra.

The fourth library was an IgG subtraction library, prepared by using a subtraction partner, generated by PCR amplification of a cDNA clone which encoded an IgG molecule. See, e.g., Ace et al, Endocrinology 134: 1305–1309 (1994), and incorporated by reference in its entirety.

This is done to eliminate any false, positive signals resulting from interaction of cDNA clones which encode IgG, with the IgG then interacting with the anti-human IgG used in the assay, as described infra. PCR product was biotinylated, and hybridized with denatured second strand cDNA, at 68° C. for 18 hours. Biotinylated hybrid molecules were coupled to streptavidin, and then removed by phenol chloroform extraction. Any remaining cDNA was also ligated into λZAP. All libraries were amplified, prior to immunoscreening discussed infra.

EXAMPLE 2

Immunoscreening was carried out, using sera obtained from patients undergoing routine diagnostic and therapeutic procedures. The sera were stored at −70° C. prior to use. Upon thawing, the sera were diluted at 1:10 in Tris buffered saline (pH 7.5), and were then passed through Sepharose 4B columns. First, the sera were passed through columns which had *E. coli* Y1090 lysates coupled thereto, and then lysates from bacteriophage infected *E. coli* BNN97 lysates. Final serum dilutions were then prepared in 0.2% non-fat dried milk/Tris buffered saline.

The method of Sahin et al., *Proc. Natl. Acad. Sci. USA* 92: 11810–11813 (1995), and U.S. Pat. No. 5,698,396, both of which are incorporated by reference, was used, with some modifications. Specifically, recombinant phages at a concentration of 4×10³ phages per 15 cm plate (pfus), were amplified for six hours, after which they were transferred to nitrocellulose membranes for 15 hours. Then, the membranes were blocked with 5% nonfat dried milk.

As an alternative to the IgG subtraction, discussed supra, membranes were prescreened in a 1:2000 dilution of peroxidase conjugated, Fc fragment specific goat anti-human IgG, for one hour, at room temperature. Color was developed using 3,3'-diaminobenzidine tetrahydrochloride, which permitted scoring of IgG encoding clones.

Membranes were then incubated in 1:100 dilutions of autologous sera, which had been pretreated with the Sepharose 4B columns, as described supra. The filters were then incubated, in a 1:3000 dilution of alkaline phosphatase conjugated Fc fragment specific, goat anti-human IgG, for one hour, at room temperature. The indicator system 4-nitroblue tetrazolium chloride/5-bromo-4-chloro-3-indolyl-phosphate was then added, and color development assessed. Any positive clones were subcloned, and retested, except the tine on the nitrocellulose membrane was reduced to three hours. A total of forty-eight positive clones were identified.

Analysis of probes for SEQ ID NOS: 1 and 2 confirmed their universal expression.

EXAMPLE 3

Example 2 described work using autologous serum. The positive clones were then rescreened, using allogeneic serum, following the same method discussed supra, in example 2, except IgG prescreening was omitted. The allogeneic sera was obtained from sixteen normal blood donors, and twenty nine patients who had been diagnosed with colorectal cancer.

The analysis with the two types of serum revealed that fourteen reacted with a subset of sera from normal and cancer patients, twenty-eight only with autologous sera, and six with both allogeneic and autologous sera. Over 60% of the allogeneic serum samples tested reacted with at least one of these positive clones. About 20% reacted with two or more.

EXAMPLE 4

In view of the results described in example 3, further experiments were carried out using serum samples from patients with other forms of cancer, i.e., renal cancer (13 samples), lung cancer (23 samples), and breast cancer (10 samples). The results are set forth in Table I which follows:

| Clone Number | Normal Sera | Colon Cancer | Renal Cancer | Lung Cancer | Breast Cancer |
| --- | --- | --- | --- | --- | --- |
| NY-Co-8 | 0/16 | 8/29 | 1/13 | 0/23 | 0/10 |
| NY-Co-9 | 0/16 | 5/29 | 1/13 | 1/23 | 0/10 |
| NY-Co-13 | 0/16 | 5/29 | 0/13 | 0/23 | 0/10 |
| NY-Co-16 | 0/16 | 3/29 | 0/13 | 0/23 | 0/10 |
| NY-Co-20 | 0/16 | 4/29 | 0/13 | 0/23 | 0/10 |
| NY-Co-38 | 0/16 | 4/29 | 3/13 | 0/23 | 1/10 |

These are referred to hereafter as SEQ ID NO:1 (NY-CO-8), SEQ ID NO:2 (NY-CO-9), SEQ ID NO:3 (NY-CO-16) and SEQ ID NO:4 (NY-CO-38),

EXAMPLE 5

Following the screening work described supra, the cDNA inserts were purified and sequenced, following standard methods.

Of the six clones which were identified as being reactive with autologous and allogeneic cancer serum, and not with normal serum, two were found to be identical to previously identified molecules. Four others were found to have little or no homology to known sequences. These are presented as SEQ ID NOS:1–4. Of twenty seven allogeneic colon cancer serum samples tested, 67% reacted with at least one of these antigens.

EXAMPLE 6

The expression pattern of MRNA corresponding to SEQ ID NOS:1, 2 and 4, as well as other sequences identified via the preceding examples was determined. To do this, RT-PCR was carried out on a panel of RNA samples, taken from normal tissue. The panel contained RNA of lung, testis, small intestine, colon, breast, liver and placenta tissues. The RNA was purchased from a commercial source. RNA from a colon tumor sample was also included. All samples were set up for duplicate runs, so that genomic DNA contamination could be accounted for. In the controls, no reverse transcriptase was used.

Primers were designed which were specific for the cDNA, which would amplify 5'-fragments, from 300 to 400 base pairs in length. The PCR reactions were undertaken at an annealing temperature of 68° C. Where appropriate, 5' and 3'-RACE reactions were undertaken, using gene specific primers, and adapter primers, together with commercially available reagents. Specifically, SEQ ID NOS:2 and 4 were tested using RACE. The resulting products were subcloned into vector pCR 2.1, screened via PCR using internal primers, and then sequenced.

SEQ ID NOS:1 and 2 were found to be amplified in all tissues tested. SEQ ID NO:4 was found in colon tumor, colon metastasis, gastric cancer, renal cancer and colon cancer cell lines Colo 204 and HT29, as well as in normal colon, small intestine, brain, stomach, testis, pancreas, liver, lung, heart, fetal brain, mammary gland, bladder, adrenal gland tissues. It is was not found in normal uterine, skeletal muscle, peripheral blood lymphocytes, placental, spleen thymus, or esophagus tissue, nor in lung cancer.

The analysis also identified differential expression of a splice variant of SEQ ID NO:4, i.e., SEQ ID NO:5. When the two sequences were compared, it was found that SEQ ID NO:4 encodes a putative protein of 652 amino acids, and molecular weight of 73,337 daltons. SEQ ID NO:5, in contrast, lacks an internal 74 base pairs, corresponding to nucleotides 1307–1380 of SEQ ID NO:4. The deletion results in formation of a stop codon at the splice function, and a putative protein of 404 amino acids, and molecular weight 45,839. The missing segment results in the putative protein lacking a PEST protein degradation sequence, thereby suggesting a longer half life for this protein.

In additional experiments, primers designed not to differentiate between SEQ ID NOS:4 and 5 resulted in almost universal amplification (placenta being the only exception). In contrast, when primers specific for SEQ ID NO:5 were used differences were seen in normal pancreatic, liver, lung, heart, fetal brain, mammary gland, bladder, and adrenal gland tissue, where there was no expression of SEQ ID NO:5 found.

EXAMPLE 7

Northern blotting was also carried out for SEQ ID NOS: 1, 2, 4 and 5. To do this, the same commercially available RNA libraries discussed supra were used.

Samples (2 μg) of polyA$^+$ RNA were analyzed from these samples, using random, $^{32}$P labelled probes 300–360 nucleotides in length, obtained from PCR products. These probes were hybridized to the RNA, for 1.5 hours, at 68° C., followed by two washes at 0.1×SSC, 0.1% SDS, 68° C., for 30 minutes each time.

SEQ ID NOS: 1 and 2 were again found to be universally expressed.

EXAMPLE 8

Further screening identified additional isoforms of SEQ ID NOS:1 and 4. These are set forth as SEQ ID NOS:6, 7, 8 and 9. The isoforms represented by SEQ ID NO:6 is a naturally occurring splice variant of SEQ ID NO: 1, found in normal colon. SEQ ID NO:7, which is an isoform of SEQ ID NO:4, was found in brain tissue, primarily spinal chord and medulla. SEQ ID NO:8, was found in normal kidney and in colon tumors, metastasized colon cancer, renal cancer, gastric cancer, and in colon cancer cell line Colo 205. It was not found in any normal tissue other than kidney.

The nucleic acid molecule whose nucleotide sequence set forth as SEQ ID NO:9, is a further isoform of SEQ ID NO:4. It is similar to SEQ ID NO:8, except it contains a long nucleotide insert encoding a loner COOH terminus. It was expressed in normal bladder and kidney cells, and renal cancer cells. It was not expressed in colon cancer cells.

It is reported in example 3, supra, that fourteen clones reacted with subsets of serum from both normal and cancer patients, while twenty eight reacted with autologous sera only. These clones were sequenced, in accordance with standard, art recognized methods. Of the clones which reacted only with autologous sera, nine appear to be previously unidentified sequences. These are set forth as SEQ ID NOS:10–18. SEQ ID NO:10 is 1445 nucleotides long, and shows some similarity to known sequences for myosin and tropomyosin. SEQ ID NO:11, which is 1226 nucleotides long, contains a TPR motif. The sequence set forth in SEQ ID NO:12 is 1857 nucleotides long, and shows similarity to cyclophillins. The nucleotide sequence set forth in SEQ ID NO:13 is 1537 nucleotides long, and shows similarity to murine gene 22A3, which has unknown function, but resembles an unconventional form of myosin, as well as an EST for heat shock inducible mRNA. As for the molecule set forth in SEQ ID NO:14, it appears to resemble a nucleic targeting signal protein. SEQ ID NO:15 is 604 nucleotides long, and may encode a lysosymol protein. The molecule set forth in SEQ ID NO:16 is 742 nucleotides long, and encodes a protein with an SH3 domain and which shows some similarity to GRB2 and human neutrophil oxidase factor. The molecule set forth in SEQ ID NO:17 is 1087 nucleotides long, and encodes a protein which contains coiled core domains. The molecule set forth in SEQ ID NO:18 is 2569 nucleotides long, shows some similarity with Drosophila homeotic maternal tudor protein, and has a DY(F)GN repeat.

Additional sequences were identified which were expressed in both normal sera and cancer cells. The sequence set forth in SEQ ID NO:19, e.g., is 2077 nucleotides long, and was expressed by both colorectal cancer and normal cells. Analysis of the sequence showed that it possesses a nuclear targeting sequence. The molecule set forth in SEQ ID NO:20 is 3309 nucleotides long, was expressed by colorectal cancer and normal cells, and is similar to heat shock protein 110 family members. The molecule presented in SEQ ID NO:21 was expressed in a colon to lung metastasis, as well as by normal tissue. It is 2918 nucleotides in length. Analysis shows that it contains 2 zinc finger domains. The nucleotide sequence of SEQ ID NO:22 was also expressed in a colon to lung metastasis, is 1898 nucleotides long, and is also expressed by normal tissue. Specifically, the reactivity of the molecules was as follows:

| SEQ ID NO: | Normal Sera Reactivity | Tumor Sera Reactivity |
| --- | --- | --- |
| 19 | 2/16 | 2/16 |
| 20 | 2/16 | 3/16 |
| 21 | 2/16 | 2/16 |
| 22 | 2/8 | 1/16 |

EXAMPLE 9

A more extensive set of experiments were carried out to study the expression pattern of SEQ ID NOS: 4, 5, 8 and 9. The methodology employed was that set out in example 6, supra. The results follow.

|  | SEQ ID NO: 4 | SEQ ID NO: 5 | SEQ ID NO: 8 | SEQ ID NO: 9 |
| --- | --- | --- | --- | --- |
| kidney | + | Negative | Negative | Negative |
| colon | + | Negative | Negative | Negative |

-continued

|  | SEQ ID NO: 4 | SEQ ID NO: 5 | SEQ ID NO: 8 | SEQ ID NO: 9 |
|---|---|---|---|---|
| small intest. | + | Negative | Negative | Negative |
| brain | + | Negative | Negative | Negative |
| stomach | + | Negative | Negative | Negative |
| testis | + | Negative | Negative | Negative |
| pancreas | + | Negative | Negative | Negative |
| lung | + | Negative | Negative | Negative |
| liver | + | Negative | Negative | Negative |
| heart | + | Negative | Negative | Negative |
| fetal brain | + | Negative | Negative | Negative |
| mammary gland | + | Negative | Negative | Negative |
| bladder | + | Negative | Negative | Negative |
| adrenal gland | + | Negative | Negative | Negative |
| uterus | Negative | Negative | Negative | Negative |
| skeletal muscle | Negative | Negative | Negative | Negative |
| PBL | Negative | Negative | Negative | Negative |
| placenta | Negative | Negative | Negative | Negative |
| spleen | Negative | Negative | Negative | Negative |
| thymus | Negative | Negative | Negative | Negative |
| esophagus | Negative | Negative | Negative | Negative |
| Tumor Tissue |  |  |  |  |
| renal cancer (4) | + (2/4) | + (2/4) | + (2/4) | + (2/4) |
| colon primary tumors (10) | + (10/10) | + (10/10) | + (10/10) | Negative |
| colon mets (4) | + (4/4) | + (4/4) | + (4/4) | Negative |
| breast cancer (6) | + (3/6) | Negative | Negative | Negative |
| lung cancer (6) | + (6/6) | Negative | Negative | Negative |
| gastric cancer (1) | + | + | + | Not tested |
| colon cancer cell lines |  |  |  |  |
| colo 205 | + | + | + | Negative |
| HT29 | + | + | Negative | Negative |
| HCT15 | Negative | Negative | Negative | Negative |

The foregoing examples demonstrate several features of the invention. These include diagnostic methods for determining presence of transformed cells, such as colon cancer cells, in a sample. The sample may contain whole cells or it may be, e.g., a body fluid sample, or an effusion, etc., where the sample may contain cells, but generally will contain shed antigen. The experiments indicate that there is a family of proteins, expression of which is associated with colon cancer. Hence, the invention involves, inter alia, detecting at least two of the proteins encoded by any of e.g., SEQ ID NOS:1, 2, 3, 4, 5, 8 or 9, wherein presence of these is indicative of a pathology, such as colon cancer or other type of related condition. Exemplary of the type of diagnostic assays which can be carried out are immunoassays, amplification assays (e.g., PCR), or, what will be referred to herein as a "display array". "Display array" as used herein refers to a depiction of the protein profile of a given sample. Exemplary of such displays are 2-dimensional electrophoresis, banding patterns such as SDS-gels, and so forth. Thus, one aspect of the invention involves diagnosing colon cancer or a related condition by determining protein display of a sample, wherein a determination of at least one of the proteins, or expression of their genes, is indicative of colon cancer or a related condition. There are many ways to carry out these assays. For example, as indicated herein, antibodies to the proteins were found in patient samples. One can assay for these antibodies using, e.g., the methodology described herein, or by using a purified protein or proteins or antigenic fragment thereof, and so forth. One can also assay for the protein itself, using antibodies, which may be isolated from samples, or generated using the protein and standard techniques. This antibodies can then be labeled, if desired, and used in standard immunoassays. These antibodies or oligonucleotide probes/primers may also be used to examine biopsied tissue samples, e.g., to diagnose precancerous conditions, early stage cancers, and so forth.

Similarly, any and all nucleic acid hybridization systems can be used, including amplification assays, such as PCR, basic probe hybridization assays, and so forth. The antibodies, such as polyclonal antibodies, monoclonal antibodies, the hybridomas which produce them, recombinantly produced antibodies, binding fragments of these, hybridization kits, DNA probes, and so forth, are all additional features of the invention.

Any of these assays can also be used in progression/regression studies. One can monitor the course of an abnormality such as colon cancer which involve expression of any one of the proteins, the expression of which is governed by the nucleic acid molecules SEQ ID NOS:1–5, simply by monitoring levels of the protein, its expression, and so forth using any or all of the methods set forth supra.

As has been indicated supra, the isolated nucleic acid molecules which comprise the nucleotide sequences set forth in SEQ ID NOS:1–8 are new, in that they have never been isolated before. These nucleic acid molecules may be used as a source to generate colon cancer specific proteins and peptides derived therefrom, and oligonucleotide probes which can themselves be used to detect expression of these genes. Hence, a further aspect of the invention is an isolated nucleic acid molecule which comprises any of the nucleotide sequences set forth in SEQ ID NOS:1–18, or molecules whose complements hybridize to one or more of these nucleotide sequences, under stringent conditions, expression vectors comprising these molecules, operatively linked to promoters, cell lines and strains transformed or transfected with these, and so forth. "Stringent conditions", is used herein, refers to condition such as those specified in U.S. Pat. No. 5,342,774, i.e., 18 hours of hybridization at 65° C., followed by four one hour washes at 2×SSC, 0.1% SDS, and a final wash at 0.2×SSC, more preferably 0.1×SSC, 0.1% SDS for 30 minutes, as well as alternate conditions which afford the same level of stringency, and more stringent conditions.

Especially preferred are those associated specifically with cancer, such as SEQ ID NOS:1, 2, 3, 4, 5, 8 and 9. It should be clear that these methodologies may also be used to track the efficacy of a therapeutic regime. Essentially, one can take a baseline value for the protein or proteins being tested, using any of the assays discussed supra, administer a given therapeutic, and then monitor levels of the protein or proteins thereafter, observing changes in protein levels as indicia of the efficacy of the regime.

The identification of the proteins and nucleic acid molecules set forth herein as being implicated in pathological conditions such as colon cancer also suggests a number of therapeutic approaches to such conditions. The experiments set forth supra establish that antibodies are produced in response to expression of these proteins, suggesting their use as a vaccine. Hence, a further embodiment of the invention is the treatment of conditions which are characterized by expression of one or more of the subject proteins, via immunotherapeutic approaches. One of these approaches is the administration of an amount of one or more these proteins, or an immunogenic peptide derived therefrom in an amount sufficient to provoke or augment an immune response. The proteins or peptides may be combined with one or more of the known immune adjuvants, such as saponins, GM-CSF, interleukins, and so forth. If the peptides are too small to generate a sufficient antibody response, they can be coupled to the well known conjugates used to stimulate responses.

Similarly, the immunotherapeutic approaches include administering an amount of inhibiting antibodies sufficient to inhibit the protein or proteins. These antibodies may be, e.g., antibodies produced via any of the standard approaches elaborated upon supra.

T cell responses may also be elicited by using peptides derived from the proteins which then complex, non-covalently, with MHC molecules, thereby stimulating proliferation of cytolytic T cells against any such complexes in the subject. It is to be noted that the T cells may also be elicited in vitro, and then reperfused into the subject being treated.

Note that the generation of T cells and/or antibodies can also be accomplished by administering cells, preferably treated to be rendered non-proliferative, which present relevant T cell or B cell epitopes for response.

The therapeutic approaches may also include gene therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the well known BCG vaccine, and so forth.

An additional DNA based therapeutic approach is the use of a vector which comprises one or more nucleotide sequences, preferably a plurality of these, each of which encodes an immunoreactive peptide derived from the expressed proteins. One can combine these peptides expressing sequences in all possible variations, such as one from each protein, several from one or more protein and one from each of the additional proteins, a plurality from some and none from others, and so forth.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated protein encoded by an isolated nucleic acid molecule selected from the group consisting of:
   (a) nucleic acid molecules which encode a cancer associated antigen, and which comprise a nucleotide sequence, the complementary sequence of which hybridizes, under stringent conditions, to at least one second nucleic acid molecule comprising a nucleotide sequence selected from the group consisting of the nucleotide sequences set forth as SEQ ID NOs:8–18,
   (b) nucleic acid molecules that differ from the nucleic acid molecules of (a) in codon sequence due to the degeneracy of the genetic code, and
   (c) full length complements of (a) or (b).

2. A composition of matter useful in stimulating an immune response to at least one protein encoded by at least one nucleic acid molecule comprising a nucleotide sequence set forth in SEQ ID NO: 8–18, said composition comprising a plurality of peptides derived from the amino acid sequence of said at least one protein, wherein said peptides bind to one or more MHC molecules presented on the surface of cells which express an abnormal amount of said at least one protein.

3. The composition of claim 2, wherein at least a portion of said plurality of peptides bind to MHC molecules and elicit a cytolytic response thereto.

4. The composition of claim 3, further comprising an adjuvant.

5. The composition of claim 4, wherein said adjuvant is a saponin, GM-CSF, or an interleukin.

6. The isolated protein of claim 1, wherein the nucleic acid molecule comprises SEQ ID NO:8.

7. The isolated protein of claim 1, wherein the nucleic acid molecule comprises SEQ ID NO:9.

8. The isolated protein of claim 1, wherein the nucleic acid molecule comprises SEQ ID NO: 10.

9. The isolated protein of claim 1, wherein the nucleic acid molecule comprises SEQ ID NO:11.

10. The isolated protein of claim 1, wherein the nucleic acid molecule comprises SEQ ID NO:12.

11. The isolated protein of claim 1, wherein the nucleic acid molecule comprises SEQ ID NO:13.

12. The isolated protein of claim 1, wherein the nucleic acid molecule comprises SEQ ID NO:14.

13. The isolated protein of claim 1, wherein the nucleic acid molecule comprises SEQ ID NO:15.

14. The isolated protein of claim 1, wherein the nucleic acid molecule comprises SEQ ID NO:16.

15. The isolated protein of claim 1, wherein the nucleic acid molecule comprises SEQ ID NO:17.

16. The isolated protein of claim 1, wherein the nucleic acid molecule comprises SEQ ID NO:18.

17. The composition of matter of claim 2, wherein the at least one nucleic acid molecule comprises the nucleotide sequence set forth in SEQ ID NO:8.

18. The composition of matter of claim 2, wherein the at least one nucleic acid molecule comprises the nucleotide sequence set forth in SEQ ID NO:9.

19. The composition of matter of claim 2, wherein the at least one nucleic acid molecule comprises the nucleotide sequence set forth in SEQ ID NO:10.

20. The composition of matter of claim 2, wherein the at least one nucleic acid molecule comprises the nucleotide sequence set forth in SEQ ID NO:11.

21. The composition of matter of claim 2, wherein the at least one nucleic acid molecule comprises the nucleotide sequence set forth in SEQ ID NO:12.

22. The composition of matter of claim 2, wherein the at least one nucleic acid molecule comprises the nucleotide sequence set forth in SEQ ID NO:13.

23. The composition of matter of claim 2, wherein the at least one nucleic acid molecule comprises the nucleotide sequence set forth in SEQ ID NO:14.

24. The composition of matter of claim 2, wherein the at least one nucleic acid molecule comprises the nucleotide sequence set forth in SEQ ID NO:15.

25. The composition of matter of claim 2, wherein the at least one nucleic acid molecule comprises the nucleotide sequence set forth in SEQ ID NO:16.

26. The composition of matter of claim 2, wherein the at least one nucleic acid molecule comprises the nucleotide sequence set forth in SEQ ID NO:17.

27. The composition of matter of claim 2, wherein the at least one nucleic acid molecule comprises the nucleotide sequence set forth in SEQ ID NO:18.

28. The composition of matter of claim 2, wherein at least one of the plurality of peptides is coupled to an immune response stimulating compound.

\* \* \* \* \*

SEQUENCE LISTING

<160> NUMBER OF SEQ ID NOS: 22

<210> SEQ ID NO 1
<211> LENGTH: 1552
<212> TYPE: DNA
<213> ORGANISM: Homo sapiens

<400> SEQUENCE: 1

```
cttctggatg catccgagaa gctaaaactt acttatgagg aaaagtgtga aattgaggaa      60
tcccaattga agtttttgag gaacgactta gctgaatatc agagaacttg tgaagatctt    120
aaagagcaac taaagcataa agaatttctt ctggctgcta atacttgtaa ccgtgttggt    180
ggtctttgtt tgaaatgtgc tcagcatgaa gctgttcttt cccaaaccca tactaatgtt    240
catatgcaga ccatcgaaag actggttaaa gaaagagatg acttgatgtc tgcactagtt    300
tccgtaagga gcagcttggc agatacgcag caaagagaag caagtgctta tgaacaggtg    360
aaacaagttt tgcaaatatc tgaggaagcc aattttgaaa aaaccaaggc tttaatccag    420
tgtgaccagt tgaggaagga gctggagagg caggcggagc gacttgaaaa agaacttgca    480
tctcagcaag agaaaagggc cattgagaaa gacatgatga aaaaggaaat aacgaaagaa    540
agggagtaca tgggatcaaa gatgttgatc ttgtctcaga atattgccca actggaggcc    600
caggtggaaa aggttacaaa ggaaaagatt tcagctatta atcaactgga ggaaattcaa    660
agccagctgg cttctcggga aatggatgtc acaaaggtgt gtggagaaat gcgctatcag    720
ctgaataaaa ccaacatgga gaaggatgag gcagaaaagg agcacagaga gttcagagca    780
aaaactaaca gggatcttga aattaaagat caggaaatag agaaattgag aatagaactg    840
gatgaaagca acaacactt ggaacaggag cagcagaagg cagccctggc cagagaggag    900
tgcctgagac taacagaact gctgggcgaa tctgagcacc aactgcacct caccagatct    960
gaaatagctc aactcagtca agaaaaaagg tatacatatg ataaattggg aaagttacag   1020
agaagaaatg aagaattgga ggaacagtgt gtccagcatg ggagagtaca tgagacgatg   1080
aagcaaaggc taaggcagct ggataagcac agccaggcca cagcccagca gctggtgcag   1140
```

-continued

| | | | |
|---|---|---|---|
| ctcctcagca | agcagaacca | gcttctcctg gagaggcaga gcctgtcgga | agaggtggac 1200 |
| cggctgcgga | cccagttacc | cagcatgcca caatctgatt gctgacctgg | atggaacaga 1260 |
| gtgaaataaa | tgaattacaa | agagatattt acattcatct ggtttagact | taatatgcca 1320 |
| caacgcacca | cgaccttccc | agggtgacac cgcctcagcc tgcagtgggg | ctggtcctca 1380 |
| tcaacgcggg | cgctgtcccc | gcacgcagtc gggctggagc tggagtctga | ctctagctga 1440 |
| gcagactcct | ggtgtatgtt | ttcagaaatg gcttgaagtt atgtgtttaa | atctgctcat 1500 |
| tcgtatgcta | ggttatacat | atgatttca ataaatgaac tttttaaaga | aa 1552 |

<210> SEQ ID NO 2
<211> LENGTH: 2885
<212> TYPE: DNA
<213> ORGANISM: Homo sapiens

<400> SEQUENCE: 2

| | | | |
|---|---|---|---|
| ggaattcctc | ttgtcgaagt | caaaggagcc cacaccaggc ggcctcaacc | attccctccc 60 |
| acagcacccc | aaatgctggg | gagcccacca tgcttctttg gaccagagtt | cccctcccca 120 |
| gagcggcccc | cctgggacgc | ctccctccta caaactgcct ttgcctgggc | cctacgacag 180 |
| tcgagacgac | ttccccctcc | gcaaaacagc ctctgaaccc aacttgaaag | tgcgttcaag 240 |
| gctaaaacag | aaggtggctg | agcggagaag cagtcccctc ctgcgtcgca | aggatgggac 300 |
| tgttattagc | acctttaaga | agagagctgt tgagatcaca ggtgccgggc | ctggggcgtc 360 |
| gtccgtgtgt | aacagcgcac | ccggctccgg ccccagctct cccaacagct | cccacagcac 420 |
| catcgctgag | aatggcttta | ctggctcagt ccccaacatc cccactgaga | tgctccctca 480 |
| gcaccgagcc | ctccctctgg | acagctcccc caaccagttc agcctctaca | cgtctccttc 540 |
| tctgcccaac | atctccctag | ggctgcaggc cacggtcact gtcaccaact | cacacctcac 600 |
| tgcctccccg | aagctgtcga | cacagcagga ggccgagagg caggccctcc | agtccctgcg 660 |
| gcagggtggc | acgctgaccg | gcaagttcat gagcacatcc tctattcctg | ctgcctgct 720 |
| gggcgtggca | ctggagggcg | acgggagccc cacgggcat gcctccctgc | tgcagcatgt 780 |
| gctgttgctg | gagcaggccc | ggcagcagag caccctcatt gctgtgccac | tccacgggca 840 |
| gtccccacta | gtgacgggtg | aacgtgtggc caccagcatg cggacggtag | gcaagctccc 900 |
| gcggcatcgg | cccctgagcc | gcactcagtc ctcaccgctg ccgcagagtc | cccaggccct 960 |
| gcagcagctg | gtcatgcaac | aacagcacca gcagttcctg gagaagcaga | agcagcagca 1020 |
| gctacagctg | ggcaagatcc | tcaccaagac aggggagctg cccaggcagc | ccaccaccca 1080 |
| ccctgaggag | acagaggagg | agctgacgga gcagcaggag gtcttgctgg | gggagggagc 1140 |
| cctgaccatg | ccccgggagg | gctccacaga gagtgagagc acacaggaag | acctggagga 1200 |
| ggaggacgag | gaagaggatg | gggaggagga ggaggattgc atccaggtta | aggacgagga 1260 |
| gggcgagagt | ggtgctgagg | agggggccga cttggaggag cctggtgctg | gatacaaaaa 1320 |
| actgttctca | gatgcccaac | cgctgcaacc tttgcaggtg taccaagcgc | ccctcagcct 1380 |
| ggccactgtg | cccaccaag | ccctgggccg tacccaatcc tcccctgctg | cccctgggg 1440 |
| catgaagaac | ccccagacc | aacccgtcaa gcacctcttc accacaagtg | tggtctacga 1500 |
| cacgttcatg | ctaaagcacc | agtgcatgtg cgggaacaca cacgtgcacc | ctgagcatgc 1560 |
| tggccggatc | cagagcatct | ggtcccggct gcaggacaca ggcctgctta | gcaagtgcga 1620 |
| gcggatccga | ggtcgcaaag | ccacgctaga tgagatccag acagtgcact | ctgaatacca 1680 |
| caccctgctc | tatgggacca | gtcccctcaa ccggcagaag ctagacagca | agaagttgct 1740 |

```
cggtcccatc agccagaaga tgtatgctgt gctgccttgt gggggcatcg gggtggacag    1800
tgacaccgtg tggaatgaga tgcactcctc cagtgctgtg cgcatggcag tgggctgcct    1860
gctggagctg gccttcaagg tggctgcagg agagctcaag aatggatttg ccatcatccg    1920
gcccccagga caccacgccg aggaatccac agccatggga ttctgcttct tcaactctgt    1980
agccatcacc gcaaaactcc tacagcagaa gttgaacgtg ggcaaggtcc tcatcgtgga    2040
ctgggacatt caccatggca atggcaccca gcaggcgttc tacaatgacc cctctgtgct    2100
ctacatctct ctgcatcgct atgacaacgg gaacttcttt ccaggctctg ggctcctga     2160 agaggttggt ggaggaccag gcgtgggta caatgtgaac gtggcatgga caggaggtgt     2220 ggacccccc attggagacg tggagtacct tacagccttc aggacagtgg tgatgcccat     2280
tgcccacgag ttctcacctg atgtggtcct agtctccgcc gggtttgatg ctgttgaagg    2340
acatctgtct cctctgggtg gctactctgt caccgccaga tgttttggcc acttgaccag    2400
gcagctgatg accctggcag ggggccgggt ggtgctggcc ctggagggag gccatgactt    2460
gaccgccatc tgtgatgcct ctgaagcttg tgtctcggct ctgctcagtg taaagctgca    2520
gcccttggat gaggcagtct tgcagcaaaa gcccaacatc aacgcagtgg ccacgctaga    2580
gaaagtcatc gagatccaga gcaaacactg gagctgtgtg cagaagttcg ccgctggtct    2640
gggccggtcc ctgcgagggg cccaagcagg tgagaccgaa gaagccgaaa tgtgaacgcc    2700
atggccttgc tgttggtggg ggccgaacag gcccaagctg cggcagcccg ggaacacagc    2760
cccaggccgg cagaggagcc catggagcag gagcctgccc tgtgacgccc cggccccat    2820 cccttttgggc ttcaccattg tgattttgtt tattttttct attaaaaaca aaagttaaa    2880 aattt                                                                2885
```

<210> SEQ ID NO 3
<211> LENGTH: 1298
<212> TYPE: DNA
<213> ORGANISM: Homo sapiens
<220> FEATURE:
<221> NAME/KEY: unsure
<222> LOCATION: 55..55
<223> OTHER INFORMATION:
<221> NAME/KEY: unsure
<222> LOCATION: 141..141
<223> OTHER INFORMATION:
<221> NAME/KEY: unsure
<222> LOCATION: 199..199
<223> OTHER INFORMATION:
<221> NAME/KEY: unsure
<222> LOCATION: 342..342
<223> OTHER INFORMATION:
<221> NAME/KEY: unsure
<222> LOCATION: 352..352
<223> OTHER INFORMATION:
<221> NAME/KEY: unsure
<222> LOCATION: 722..722
<223> OTHER INFORMATION:
<221> NAME/KEY: unsure
<222> LOCATION: 750..750
<223> OTHER INFORMATION:
<221> NAME/KEY: unsure
<222> LOCATION: 1058..1058
<223> OTHER INFORMATION:
<221> NAME/KEY: unsure
<222> LOCATION: 1101..1101
<223> OTHER INFORMATION:
<221> NAME/KEY: unsure
<222> LOCATION: 1144..1144
<223> OTHER INFORMATION:

<400> SEQUENCE: 3

-continued

```
ggctgctgaa atgactgcga accggcttgc agagagcctt ctggctttga gccancagga      60
agaactagcg gatttgccaa aagactacct cttgagtgag agtgaagatg aggggggacaa    120 tgatggagag agaaagcatc naaagcttct ggaagcaatc agttcccttg atggaaagaa    180
taggcggaaa ttggctgana ggtctgaggc tagtctgaag gtgtcagagt tcaatgtcag    240
ttctgaagga tcaggagaaa agctggtcct tgcagatctg cttgagcctg ttaaaacttc    300
atcttctttg gccactgtga aaagcaact gagtagagtc anatcaaaga anacagtgga    360
gttacctctg aacaaagaag agattgaacg gatccacaga gaatagcatt caataaaacg    420
cacaagtcct ctccaaatgg gaccctgtcg tcctgaagaa ccggcaggca gagcagctgg    480
tttttcccct ggagaaagag gagccagcca ttgctcccat tgaacatgtg ctcagtggct    540
ggaaggcaag aactcccctg gagcaggaaa ttttcaacct cctccataag aacaagcagc    600
cagtgacaga cccctttactg accctgtgg aaaaggcctc tctccgagcc atgagcctag    660
aagaggcaaa gatgcgacga gcagagcttc agagggctcg ggctctgcag tcctactatg    720
angccaaggc tcgaagagag aagaaaatcn aaagttaaaa gtatcacaaa gtcgtgaaga    780
aaggaaaggc caagaaagcc ctaaaagagt ttgagcagct gcggaaggtt aatccagctg    840
ccgcactaga agaacgaaga aaagaggaaa gaggaggag gagaaagaag aagaacaagg    900
agaagaagaa agaagaaggg agaaggagaa gaaaagaagg agaagaggaa aaggaagaag    960
gagaaagaaa aggagaagga aaaggaaaag aaggagaaga aagaagaact aagaagaagg   1020
agaggaagaa taagaaggaa agaagaaaga aaaagtnaa agaagaagaa agaaggaaga   1080
aggaaagaag aggaagaact nagaagaaga agaggaggag aagaagaaag aagaataagg   1140
aacnagaaag aaggagaaga agaataagaa agaggaagaa gaaaagaag aaaagaagaa   1200 ggaaagaagg agaaaaagga agaaaaaagg aagaagaaag tagaaagcgg aagaaagaaa   1260
agaaagtata agaaggaaga agaagaaaga aggaaaaa                           1298
```

<210> SEQ ID NO 4
<211> LENGTH: 2236
<212> TYPE: DNA
<213> ORGANISM: Homo sapiens

<400> SEQUENCE: 4

```
cctggcccgg tcgcggtcgc ggctctttcc agctcctggc agccgggcac ccgaaggaac     60
gggtcgtgca acgacgcagc tggacctggc ccagccatgg accgaaaagt ggcccgagaa   120
ttccggcata aggtggattt tctgattgaa aatgatgcag agaaggacta tctctatgat   180
gtgctgcgaa tgtaccacca gaccatggac gtggccgtgc tcgtgggaga cctgaagctg   240
gtcatcaatg aacccagccg tctgcctctg tttgatgcca ttcggccgct gatcccactg   300
aagcaccagg tggaatatga tcagctgacc ccccggcgct ccaggaagct gaaggaggtg   360
cgtctggacc gtctgcaccc cgaaggcctc ggcctgagtg tgcgtggtgg cctggagttt   420
ggctgtgggc tcttcatctc ccacctcatc aaaggcggtc aggcagacag cgtcgggctc   480
caggtagggg acgagatcgt ccggatcaat ggatattcca tctcctcctg tacccatgag   540
gaggtcatca acctcattcg aaccaagaaa actgtgtcca tcaaagtgag acacatcggc   600
ctgatccccg tgaaaagctc tcctgatgag cccctcactt ggcagtatgt ggatcagttt   660
gtgtcggaat ctgggggcgt gcgaggcagc ctgggctccc ctggaaatcg ggaaaacaag   720
gagaagaagg tcttcatcag cctggtaggc tcccgaggcc ttgctgcag catttccagc   780
```

-continued

```
ggccccatcc agaagcctgg catctttatc agccatgtga aacctggctc cctgtctgct      840
gaggtgggat tggagatagg ggaccagatt gtcgaagtca atggcgtcga cttctctaac      900
ctggatcaca aggaggctgt aaatgtgctg aaaaatagcc gcagcctgac catctccatt      960
gtagctgcag ctggccggga gctgttcatg acagaccggg agcggctggc agaggcgcgg     1020
cagcgtgagc tgcagcggca ggagcttctc atgcagaagc ggctggcgat ggagtccaac     1080
aagatcctcc aggagcagca ggagatggag cggcaaagga gaaagaaat tgcccagaag       1140
gcagcagagg aaaatgagag ataccggaag gagatggaac agattgtaga ggaggaagag     1200
aagtttaaga agcaatggga agaagactgg ggctcaaagg aacagctact cttgcctaaa     1260
accatcactg ctgaggtaca cccagtaccc cttcgcaagc caaagtatga tcagggagtg     1320
gaacctgagc tcgagcccgc agatgacctg gatggaggca cggaggagca gggagagcag     1380
gatttccgga aatatgagga aggctttgac ccctactcta tgttcacccc agagcagatc     1440
atggggaagg atgtccggct cctacgcatc aagaaggagg atccttaga cctggccctg      1500
gaaggcggtg tggactcccc cattgggaag gtggtcgttt ctgctgtgta tgagcgggga     1560
gctgctgagc ggcatggtgg cattgtgaaa ggggacgaga tcatggcaat caacggcaag     1620
attgtgacag actacaccct ggctgaggct gacgctgccc tgcagaaggc ctggaatcag     1680
ggcggggact ggatcgacct tgtggttgcc gtctgccccc caaaggagta tgacgatgag     1740
ctgaccttct tgctgaagtc caaaagggga accaaattc acgcgttagg aaacagtgag      1800
ctccggcccc aactcgtgaa cacaaagcct cggaccagcc ttgagagagg ccacatgaca     1860
cacaccagat ggcatccttg ggacctgaat ctatcaccca ggaatctcaa actcccttg     1920
gccctgaacc agggccagat aaggaacagc tcgggccact tttttgaagg ccaatgtgga     1980
ggaaagggag cagccagccg tttgggagaa gatctcaagg atccagactc tcattccttt     2040
cctctggccc agtgaatttg gtctctccca gctttggggg actccttcct tgaaccctaa     2100
taagaccccca ctggagtctc tctctctcca tccctctcct ctgccctctg ctctaattgc    2160
tgccaggatt gtcactccaa accttactct gagctcatta ataaaataaa cagatttatt    2220
ttccagctta aaaaaa                                                      2236
```

<210> SEQ ID NO 5
<211> LENGTH: 2162
<212> TYPE: DNA
<213> ORGANISM: Homo sapiens

<400> SEQUENCE: 5

```
cctggcccgg tcgcggtcgc ggctctttcc agctcctggc agccgggcac ccgaaggaac       60
gggtcgtgca acgacgcagc tggacctggc ccagccatgg accgaaaagt ggcccgagaa      120
ttccggcata aggtggattt tctgattgaa aatgatgcag agaaggacta tctctatgat      180
gtgctgcgaa tgtaccacca gaccatggac gtggccgtgc tcgtgggaga cctgaagctg     240
gtcatcaatg aacccagccg tctgcctctg tttgatgcca ttcggccgct gatcccactg      300
aagcaccagg tggaatatga tcagctgacc ccccggcgct ccaggaagct gaaggaggtg    360
cgtctggacc gtctgcaccc cgaaggcctc ggcctgagtg tgcgtggtgg cctggagttt     420
ggctgtgggc tcttcatctc ccacctcatc aaaggcggtc aggcagacag cgtcgggctc     480
caggtagggg acgagatcgt ccggatcaat ggatattcca tctcctcctg tacccatgag     540
gaggtcatca acctcattcg aaccaagaaa actgtgtcca tcaaagtgag acacatcggc     600
ctgatccccg tgaaaagctc tcctgatgag cccctcactt ggcagtatgt ggatcagttt     660
```

```
gtgtcggaat ctgggggcgt gcgaggcagc ctgggctccc ctggaaatcg ggaaaacaag      720
gagaagaagg tcttcatcag cctggtaggc tcccgaggcc ttggctgcag catttccagc      780
ggccccatcc agaagcctgg catctttatc agccatgtga aacctggctc cctgtctgct      840
gaggtgggat tggagatagg ggaccagatt gtcgaagtca atggcgtcga cttctctaac      900
ctggatcaca aggaggctgt aaatgtgctg aaaaatagcc gcagcctgac catctccatt      960
gtagctgcag ctggccggga gctgttcatg acagaccggg agcggctggc agaggcgcgg     1020
cagcgtgagc tgcagcggca ggagcttctc atgcagaagc ggctggcgat ggagtccaac     1080
aagatcctcc aggagcagca ggagatggag cggcaaagga gaaaagaaat tgcccagaag     1140
gcagcagagg aaaatgagag ataccggaag gagatggaac agattgtaga ggaggaagag     1200
aagtttaaga gcaatggga agaagactgg ggctcaaagg aacagctact cttgcctaaa     1260
accatcactg ctgaggtaca cccagtaccc cttcgcaagc caaagtgatt ccggaaata     1320 tgaggaaggc tttgacccct actctatgtt caccccagag cagatcatgg ggaaggatgt     1380
ccggctccta cgcatcaaga aggagggatc cttagacctg ccctggaag gcggtgtgga     1440 ctcccccatt gggaaggtgg tcgtttctgc tgtgtatgag cggggagctg ctgagcggca     1500
tggtggcatt gtgaaagggg acgagatcat ggcaatcaac ggcaagattg tgacagacta     1560
caccctggct gaggctgacg ctgccctgca gaaggcctgg aatcagggcg gggactggat     1620
cgaccttgtg gttgccgtct gccccccaaa ggagtatgac gatgagctga ccttcttgct     1680
gaagtccaaa aggggaaacc aaattcacgc gttaggaaac agtgagctcc ggccccacct     1740
cgtgaacaca aagcctcgga ccagccttga gagaggccac atgacacaca ccagatggca     1800
tccttgggac ctgaatctat cacccaggaa tctcaaactc cctttggccc tgaaccaggg     1860
ccagataagg aacagctcgg gccacttttt tgaaggccaa tgtggaggaa agggagcagc     1920
cagccgtttg ggagaagatc tcaaggatcc agactctcat tcctttcctc tggcccagtg     1980
aatttggtct ctcccagctt tgggggactc cttccttgaa ccctaataag accccactgg     2040
agtctctctc tctccatccc tctcctctgc cctctgctct aattgctgcc aggattgtca     2100
ctccaaacct tactctgagc tcattaataa aataaacaga tttattttcc agcttaaaaa     2160
aa                                                                    2162
```

<210> SEQ ID NO 6
<211> LENGTH: 1789
<212> TYPE: DNA
<213> ORGANISM: Homo sapiens

<400> SEQUENCE: 6

```
cttctggatg catccgagaa gctaaaactt acttatgagg aaaagtgtga aattgaggaa       60
tcccaattga agttttgag gaacgactta gctgaatatc agagaacttg tgaagatctt      120
aaagagcaac taaagcataa agaatttctt ctggctgcta atacttgtaa ccgtgttggt      180
ggtctttgtt tgaaatgtgc tcagcatgaa gctgttcttt cccaaaccca tactaatgtt      240
catatgcaga ccatcgaaag actggttaaa gaaagagatg acttgatgtc tgcactagtt      300
tccgtaagga gcagcttggc agatacgcag caaagagaag caagtgctta tgaacaggtg      360
aaacaagttt tgcaaatatc tgaggaagcc aattttgaaa aaccaaggc tttaatccag      420 tgtgaccagt tgaggaagga gctggagagg caggcggagc gacttgaaaa agaacttgca      480
tctcagcaag agaaagggc cattgagaaa gacatgatga aaaggaaat aacgaaagaa      540
```

-continued

| | |
|---|---|
| agggagtaca tgggatcaaa gatgttgatc ttgtctcaga atattgccca actgaggcc | 600 |
| caggtggaaa aggttacaaa ggaaaagatt tcagctatta atcaactgga ggaaattcaa | 660 |
| agccagctgg cttctcggga aatggatgtc acaaaggtgt gtggagaaat gcgctatcag | 720 |
| ctgaataaaa ccaacatgga aaggatgag gcagaaaagg agcacagaga gttcagagca | 780 |
| aaaactaaca gggatcttga aattaaagat caggaaatag agaaattgag aatagaactg | 840 |
| gatgaaagca aacaacactt ggaacaggag cagcagaagg cagccctggc cagagaggag | 900 |
| tgcctgagac taacagaact gctgggcgaa tctgagcacc aactgcacct caccagacag | 960 |
| gaaaaagata gcattcagca gagctttagc aaggaagcaa aggcccaagc ccttcaggcc | 1020 |
| cagcaaagag agcaggagct gacacagaag atacagcaaa tggaagccca gcatgacaaa | 1080 |
| actgaaaatg aacagtattt gttgctgacc tcccagaata cattttttgac aaagttaaag | 1140 |
| gaagaatgct gtacattagc caagaaactg aacaaatct ctcaaaaaac cagatctgaa | 1200 |
| atagctcaac tcagtcaaga aaaaggtat acatatgata aattgggaaa gttacagaga | 1260 |
| agaaatgaag aattggagga acagtgtgtc cagcatggga gagtacatga gacgatgaag | 1320 |
| caaaggctaa ggcagctgga taagcacagc caggccacag cccagcagct ggtgcagctc | 1380 |
| ctcagcaagc agaaccagct tctcctggag aggcagagcc tgtcggaaga ggtggaccgg | 1440 |
| ctgcggaccc agttacccag catgccacaa tctgattgct gacctggatg aacagagtg | 1500 |
| aaataaatga attacaaaga gatatttaca ttcatctggt ttagacttaa tatgccacaa | 1560 |
| cgcaccacga ccttcccagg gtgacaccgc ctcagcctgc agtggggctg gtcctcatca | 1620 |
| acgcgggcgc tgtccccgca cgcagtcggg ctggagctgg agtctgactc tagctgagca | 1680 |
| gactcctggt gtatgttttc agaaatggct tgaagttatg tgtttaaatc tgctcattcg | 1740 |
| tatgctaggt tatacatatg attttcaata atgaactttt ttaaagaaa | 1789 |

<210> SEQ ID NO 7
<211> LENGTH: 1306
<212> TYPE: DNA
<213> ORGANISM: Homo sapiens

<400> SEQUENCE: 7

| | |
|---|---|
| aaaaatagcc gcagcctgac catctccatt gtagctgcag ctggccggga gctgttcatg | 60 |
| acagaccggg agcggctggc agaggcgcgg cagcgtgagc tgcagcggca ggagcttctc | 120 |
| atgcagaagc ggctggcgat ggagtccaac aagatcctcc aggagcagca ggagatggag | 180 |
| cggcaaagga gaaagaaat tgcccagaag gcagcagagg aaaatgagag ataccggaag | 240 |
| gagatggaac agattgtaga ggaggaagag aagtttaaga agcaatggga agaagactgg | 300 |
| ggctcaaagg aacagctact cttgcctaaa accatcactg ctgaggtaca cccagtaccc | 360 |
| cttcgcaagc caaagtatga tcagggagtg gaacctgagc tcgagcccgc agatgacctg | 420 |
| gatggaggca cggaggagca gggagagcag gatttccgga aatatgagga aggctttgac | 480 |
| ccctactcta tgttcacccc agagcagatc atggggaagg atgtccggct cctacgcatc | 540 |
| aagaaggagg gatccttaga cctggccctg gaaggcggtg tggactcccc cattgggaag | 600 |
| gtggtcgttt ctgctgtgta tgagcgggga gctgctgagc ggcatggtgg cattgtgaaa | 660 |
| ggggacgaga tcatggcaat caacggcaag attgtgacag actacaccct ggctgaggct | 720 |
| gacgctgccc tgcagaaggc ctggaatcag ggcgggact ggatcgacct tgtggttgcc | 780 |
| gtctgccccc caaaggagta tgacgatgag ctgacctct tgctgaagtc caaaggggaa | 840 |
| aaccaaattc acgcgttagg aaacagtgag ctccggcccc acctcgtgaa cacaaagcct | 900 |

```
cggaccagcc ttgagagagg ccacatgaca cacaccagat ggcatccttg ggacctgaat    960
ctatcaccca ggaatctcaa actcccttrg gccctgaacc agggccagat aaggaacagc   1020
tcgggccact tttttgaagg ccaatgtgga ggaaagggag cagccagccg tttgggagaa   1080
gatctcaagg atccagactc tcattccttt cctctggccc agtgaatttg gtctctccca   1140
gctttggggg actccttcct tgaacccraa taagacccca ctggagtctc tctctctcca   1200
tccctctcct ctgccctctg ctctaattgc tgccaggatt gtcactccaa accttactct   1260
gagctcatta ataaaataaa cagatttatt ttccagctta aaaaaa                  1306

<210> SEQ ID NO 8
<211> LENGTH: 2289
<212> TYPE: DNA
<213> ORGANISM: Homo sapiens

<400> SEQUENCE: 8
cctgccccgg tcgcggtcgc ggctctttcc agctcctggc agccgggcac ccgaaggaac     60
gggtcgtgca acgacgcagc tggacctggc ccagccatgg accgaaaagt ggcccgagaa    120
ttccggcata aggtggattt tctgattgaa aatgatgcag agaaggacta tctctatgat    180
gtgctgcgaa tgtaccacca gaccatggac gtggccgtgc tcgtgggaga cctgaagctg    240
gtcatcaatg aacccagccg tctgcctctg tttgatgcca ttcggccgct gatcccactg    300
aagcaccagg tggaatatga tcagctgacc ccccggcgct ccaggaagct gaaggaggtg    360
cgtctggacc gtctgcaccc cgaaggcctc ggcctgagtg tgcgtggtgg cctggagttt    420
ggctgtgggc tcttcatctc ccacctcatc aaaggcggtc aggcagacag cgtcgggctc    480
caggtagggg acgagatcgt ccggatcaat ggatattcca tctcctcctg tacccatgag    540
gaggtcatca acctcattcg aaccaagaaa actgtgtcca tcaaagtgag acacatcggc    600
ctgatccccg tgaaaagctc tcctgatgag cccctcactt ggcagtatgt ggatcagttt    660
gtgtcggaat ctgggggcgt gcgaggcagc ctgggctccc ctggaaatcg ggaaaacaag    720
gagaagaagg tcttcatcag cctggtaggc tcccgaggcc ttggctgcag catttccagc    780
ggccccatcc agaagcctgg catctttatc agccatgtga acctggctc cctgtctgct    840
gaggtgggat tggagatagg ggaccagatt gtcgaagtca atggcgtcga cttctctaac    900
ctggatcaca aggaggctgt aaatgtgctg aaaaatagcc gcagcctgac catctccatt    960
gtagctgcag ctggccggga gctgttcatg acagaccggg agcggctggc agaggcgcgg   1020
cagcgtgagc tgcagcggca ggagcttctc atgcagaagc ggctggcgat ggagtccaac   1080
aagatcctcc aggagcagca ggagatggag cggcaaagga gaaagaaat tgcccagaag   1140
gcagcagagg aaaatgagag ataccggaag gagatggaac agattgtaga ggaggaagag   1200
aagtttaaga gcaatggga gaagactgg ggctcaaagg aacagctact cttgcctaaa   1260
accatcactg ctgaggtaca cccagtaccc cttcgcaagc caagtatga tcagggagtg   1320
gaacctgagc tcgagcccgc agatgacctg gatgaaggca cggaggagca gggagagcag   1380
ccacaggaga tgttgaagag gatggtggtt tatcaagaca gcattcaaga caagatttcc   1440
ggaaatatga ggaaggcttt gaccccract ctatgttcac cccagagcag atcatgggga   1500
aggatgtccg gctcctacgc atcaagaagg agggatcctt agacctggcc ctggaaggcg   1560
gtgtggactc ccccattggg aagtggtcg ttctgctgt gtatgagcgg ggagctgctg   1620
agcggcatgg tggcattgtg aaaggggacg agatcatggc aatcaacggc aagattgtga   1680
```

-continued

| | |
|---|---|
| cagactacac cctggctgag gctgacgctg ccctgcagaa ggcctggaat cagggcgggg | 1740 |
| actggatcga ccttgtggtt gccgtctgcc ccccaaagga gtatgacgat gagctgacct | 1800 |
| tcttgctgaa gtccaaaagg ggaaaccaaa ttcacgcgtt aggaaacagt gagctccggc | 1860 |
| cccacctcgt gaacacaaag cctcggacca gccttgagag aggccacatg acacacacca | 1920 |
| gatggcatcc ttgggacctg aatctatcac ccaggaatct caaactccct ttggccctga | 1980 |
| accagggcca gataaggaac agctcgggcc acttttttga aggccaatgt ggaggaaagg | 2040 |
| gagcagccag ccgtttggga gaagatctca aggatccaga ctctcattcc tttcctctgg | 2100 |
| cccagtgaat ttggtctctc ccagctttgg gggactcctt ccttgaaccc taataagacc | 2160 |
| ccactggagt ctctctctct ccatccctct cctctgccct ctgctctaat tgctgccagg | 2220 |
| attgtcactc caaaccttac tctgagctca ttaataaaat aaacagattt attttccagc | 2280 |
| ttaaaaaaa | 2289 |

<210> SEQ ID NO 9
<211> LENGTH: 2409
<212> TYPE: DNA
<213> ORGANISM: Homo sapiens

<400> SEQUENCE: 9

| | |
|---|---|
| cctggcccgg tcgcggtcgc ggctcttcc agctcctggc agccgggcac ccgaaggaac | 60 |
| gggtcgtgca acgacgcagc tggacctggc ccagccatgg accgaaaagt ggcccgagaa | 120 |
| ttccggcata aggtggattt tctgattgaa aatgatgcag agaaggacta tctctatgat | 180 |
| gtgctgcgaa tgtaccacca gaccatggac gtggccgtgc tcgtgggaga cctgaagctg | 240 |
| gtcatcaatg aacccagccg tctgcctctg tttgatgcca ttcggccgct gatcccactg | 300 |
| aagcaccagg tggaatatga tcagctgacc ccccggcgct ccaggaagct gaaggaggtg | 360 |
| cgtctggacc gtctgcaccc cgaaggcctc ggcctgagtg tgcgtggtgg cctggagttt | 420 |
| ggctgtgggc tcttcatctc ccacctcatc aaaggcggtc aggcagacag cgtcgggctc | 480 |
| caggtagggg acgagatcgt ccggatcaat ggatattcca tctcctcctg tacccatgag | 540 |
| gaggtcatca acctcattcg aaccaagaaa actgtgtcca tcaaagtgag acacatcggc | 600 |
| ctgatccccg tgaaaagctc tcctgatgag cccctcactt ggcagtatgt ggatcagttt | 660 |
| gtgtcggaat ctggggggcgt gcgaggcagc ctgggctccc ctggaaatcg ggaaaacaag | 720 |
| gagaagaagg tcttcatcag cctggtaggc tcccgaggcc ttggctgcag catttccagc | 780 |
| ggccccatcc agaagcctgg catctttatc agccatgtga acctggctc cctgtctgct | 840 |
| gaggtgggat ggagataggg gaccagatt gtcgaagtca atggcgtcga cttctctaac | 900 |
| ctggatcaca aggaggctgt aaatgtgctg aaaaatagcc gcagcctgac catctccatt | 960 |
| gtagctgcag ctggccggga gctgttcatg acagaccggg agcggctggc agaggcgcgg | 1020 |
| cagcgtgagc tgcagcggca ggagcttctc atgcagaagc ggctggcgat ggagtccaac | 1080 |
| aagatcctcc aggagcagca ggagatggag cggcaaagga gaaagaaat tgcccagaag | 1140 |
| gcagcagagg aaaatgagag ataccggaag gagatggaac agattgtaga ggaggaagag | 1200 |
| aagtttaaga agcaatggga agaagactgg ggctcaaagg aacagctact cttgcctaaa | 1260 |
| accatcactg ctgaggtaca cccagtaccc cttcgcaagc caaagtatga tcaggagtg | 1320 |
| gaacctgagc tcgagcccgc agatgacctg gatggaggca cggaggagca gggagagcag | 1380 |
| acattttgcc caagcccaca gcctccacga ggccctggcc tgtccaccat ctccaaacct | 1440 |
| gtcatggtcc accaggagcc caatttcatc tacaggccag ctgtgaaatc tgaagttctg | 1500 |

-continued

| | |
|---|---|
| ccacaggaga tgttgaagag gatggtggtt tatcaagaca gcattcaaga caagatttcc | 1560 |
| ggaaatatga ggaaggcttt gaccccta ctatgttcac cccagagcag atcatgggga | 1620 |
| aggatgtccg gctcctacgc atcaagaagg agggatcctt agacctggcc ctggaaggcg | 1680 |
| gtgtggactc ccccattggg aagtggtcg tttctgctgt gtatgagcgg ggagctgctg | 1740 |
| agcggcatgg tggcattgtg aaaggggacg agatcatggc aatcaacggc aagattgtga | 1800 |
| cagactacac cctggctgag gctgacgctg ccctgcagaa ggcctggaat cagggcgggg | 1860 |
| actggatcga ccttgtggtt gccgtctgcc ccccaaagga gtatgacgat gagctgacct | 1920 |
| tcttgctgaa gtccaaaagg ggaaaccaaa ttcacgcgtt aggaaacagt gagctccggc | 1980 |
| cccacctcgt gaacacaaag cctcggacca gccttgagag aggccacatg acacacacca | 2040 |
| gatggcatcc ttgggacctg aatctatcac ccaggaatct caaactccct ttggccctga | 2100 |
| accagggcca gataaggaac agctcgggcc acttttttga aggccaatgt ggaggaaagg | 2160 |
| gagcagccag ccgtttggga agatctca aggatccaga ctctcattcc tttcctctgg | 2220 |
| cccagtgaat ttggtctctc ccagctttgg gggactcctt ccttgaaccc taataagacc | 2280 |
| ccactggagt ctctctctct ccatccctct cctctgccct ctgctctaat tgctgccagg | 2340 |
| attgtcactc caaaccttac tctgagctca ttaataaaat aaacagattt attttccagc | 2400 |
| ttaaaaaaa | 2409 |

<210> SEQ ID NO 10
<211> LENGTH: 1445
<212> TYPE: DNA
<213> ORGANISM: Homo sapiens
<220> FEATURE:
<221> NAME/KEY: unsure
<222> LOCATION: 1287..1287
<223> OTHER INFORMATION:
<221> NAME/KEY: unsure
<222> LOCATION: 1309..1309
<223> OTHER INFORMATION:
<221> NAME/KEY: unsure
<222> LOCATION: 1359..1359
<223> OTHER INFORMATION:

<400> SEQUENCE: 10

| | |
|---|---|
| ctccggcagg gagtcctagc gcagactttg cggttcatgg agagtctctg ggagacaggc | 60 |
| acctgcggac gctgcagata agttacgacg cactgaaaga tgaaaattct aagctgagaa | 120 |
| gaaagctgaa tgaggttcag agcttctctg aagctcaaac agaaatggtg aggacgcttg | 180 |
| agcggaagtt agaagcaaaa atgatcaagg aggaaagcga ctaccacgac ctggagtcgg | 240 |
| tggttcagca ggtggagcag aacctggagc tgatgaccaa acgggctgta aaggcagaaa | 300 |
| accacgtcgt gaaactaaaa caggaaatca gtttgctcca ggcgcaggtc tccaacttcc | 360 |
| agcgagagaa tgaagccctg cggtgcggcc agggtgccaa cctgaccgtg gtgaagcaga | 420 |
| acgccgacgt ggccctgcag aacctccggg tggtcatgaa cagtgcacag gcttccatca | 480 |
| agcaactggt ttccggagct gagacactga atcttgttgc cgaaatcctt aaatctatag | 540 |
| acagaatttc tgaagttaaa gacgaggagg aagactcttg aggacccctg ggtgttctca | 600 |
| gcatgaagct ccgtgtatac cctgaggtca ccaccgctcg atctaaatgt gcagttgtgt | 660 |
| ccttaaatat gcagtcttca cccagagtaa agtgttgatc gcaagagtcc agtgtcgtgc | 720 |
| cctcagccag ttcttggcca ccacaatggg agcagccctg gccgagttgt ctctgtggtt | 780 |
| tctatgcagc ccttcttggc gaaattcctg cgatcttata gattctaatg agctcttgga | 840 |

-continued

```
agacattgtc ataaaagcca gtgatttttaa gaaaaagagt ggttctggaa tcaatgttttt      900 ccagtcccat cccagaacat cagttgtaag ataagtacaa ttggttgtcc ttgatttcat       960
aagtagaaca acactaaat gtgcctctga gatggccacc ccgggcaggg acctgtgcct       1020
tccgccgatg ctcagggctc cctctggctc ccgggtcact cttgtggccc cagtgggtgg      1080
tccctgcagt catggcctga gtgcgcaggg gccaccgcgt ggctgctgct gtcctcctcc      1140
ggggaccacg ggggaacaag gtcacacctt ccgtgctgtg aagctgtcca gatgtgcctc      1200
tttggctggg ggttttggtg gacgtttcaa gtggcatttt gtacaatgca ggttagaatt      1260
caggaatttc aagtatgtgc ccgggtntgt caggtcccag ttgcctttnt gacggcccccc    1320 ctcagaggga cggcgatgag cactaaatgc tttttttgant attttcctat agattttttt     1380
taaaactttt ttttcctcct gttccaattg atagctttct tatttaataa attctgtagt     1440
tcacc                                                                 1445
```

<210> SEQ ID NO 11
<211> LENGTH: 1226
<212> TYPE: DNA
<213> ORGANISM: Homo sapiens

<400> SEQUENCE: 11

```
ctgggccgcg aggcgcggag cttgggagcg gagcccaggc cgtgccgcgc ggcgccatga       60
agggcaagga ggagaaggag ggcggcgcac ggctgggcgc tggcggcgga agccccgaga     120
agagcccgag cgcgcaggag ctcaaggagc agggcaatcg tctgttcgtg ggccgaaagt     180
acccggaggc ggcggcctgc tacggccgcg cgatcacccg gaacccgctg gtggccgtgt     240
attacaccaa ccgggccttg tgctacctga agatgcagca gcacgagcag gccctggccg     300
actgccggcg cgccctggag ctggacgggc agtctgtgaa ggcgcacttc ttcctggggc     360
agtgccagct ggagatggag agctatgatg aggccatcgc caatctgcag cgagcttaca     420
gcctggccaa ggagcagcgg ctgaacttcg gggacgacat ccccagcgct cttcgaatcg     480
cgaagaagaa gcgctggaac agcattgagg agcggcgcat ccaccaggag agcgagctgc     540
actcctacct ctccaggctc attgccgcgg agcgtgagag ggagctggaa gagtgccagc     600
gaaaccacga gggtgatgag gacgacagcc acgtccgggc ccagcaggcc tgcattgagg     660
ccaagcacga caagtacatg gcggacatgg acagcttttt ttctcaggtg gatgagaaga     720
ggaagaagcg agacatcccc gactaccgtgt gtggcaagat cagctttgag ctgatgcggg     780
agccgtgcat cacgcccagt ggcatcacct acgaccgcaa ggacatcgag gagcacctgc     840
agcgtgtggg tcatttttgac ccggtgaccg ggagcccccct gacccaggaa cagttcatcc     900
ccaacttggc tatgaaggag gttattgacg cattcatctc tgagaatggc tgggtggagg     960
actactgagg ttccctgccc tacctggcgt cctggtccag gggagccctg ggcagaagcc    1020 cccggccccct aaacatagtt tatgttttttg gccacccccga ccgcttcccc caagttctgc    1080
tgttggactc tggactgttt cccctctcag catcgctttt gctgggccgt gattgtcccc     1140
tttgtgggct ggaaaagcag gtgagggtgg gctgggctga ggccattgcc gccactatct    1200
gtgtaataaa atccgtgagc acgaaa                                         1226
```

<210> SEQ ID NO 12
<211> LENGTH: 1857
<212> TYPE: DNA
<213> ORGANISM: Homo sapiens
<220> FEATURE:
<221> NAME/KEY: unsure
<222> LOCATION: 96..96

<223> OTHER INFORMATION:

<400> SEQUENCE: 12

```
gtgaggggct cctttgggca ggggtagtgt ttggtgtccc tgtcttgcgt gatattgaca      60
aactgaagct ttcctgcacc actggactta aggaanagtg tactcgtagg cggacagctt     120
tagtggccgg ccggccgctc tcatccccg taaggagcag agtcctttgt actgaccaag      180
atgagcaaca tctacatcca ggagcctccc acgaatggga aggttttatt gaaaactaca     240
gctggagata ttgacataga gttgtggtcc aagaagctc ctaaagcttg cagaaatttt      300
atcccaactt tgtttggaag cttattatga caataccatt tttcatagag ttgtgcctgg     360
tttcatagtc caaggcggag atcctactgg cacagggagt ggtggagagt ctatctatgg     420
agcgccattc aaagatgaat tcattcacg gttgcgtttt aatcggagag gactggttgc      480
catggcaaat gctggttctc atgataatgg cacccacttt ttcttcacac tgggtcgagc     540
agatgaactt aacaataagc ataccatctt tggaaaggtt acaggggata cagtatataa     600
catgttgcga ctgtcagaag tagacattga tgatgacgaa agaccacata atccacacaa     660
aataaaaagc tgtgaggttt tgtttaatcc ttttgatgac atcattccaa gggaaattaa     720
aaggctgaaa aaagagaaac cagaggagga agtaaagaaa ttgaaaccca aaggcacaaa     780
aaattttagt ttactttcat ttggagagga agctgaggaa gaagaagagg aagtaaatcg     840
agttagtcag agcatgaagg gcaaaagcaa aagtagtcat gacttgctta aggatgatcc     900
acatctcagt tctgttccag ttgtagaaag tgaaaaaggt gatgcaccag atttagttga     960
tgatggagaa gatgaaagtg cagagcatga tgaatatatt gatggtgatg aaaagaacct    1020
gatgagagaa agaattgcca aaaattaaa aaggacaca agtgcgaatg ttaaatcagc      1080
tggagaagga gaagtggaga agaaatcagt cagccgcagt gaagagctca gaaaagaagc    1140
aagacaatta aaacgggaac tcttagcagc aaaacaaaaa aagtagaaa atgcagcaaa     1200
acaagcagaa aaaagaagtg aagaggaaga agcccctcca gatggtgctg ttgccgaata    1260
cagaagagaa aagcaaaagt atgaagcttt gaggaagcaa cagtcaaaga agggaacttc    1320
ccgggaagat cagacccttg cactgctgaa ccagtttaaa tctaaactca ctcaagcaat    1380
tgctgaaaca cctgaaaatg acattcctga aacagaagta gaagatgatg aaggatggat    1440
gtcacatgta cttcagtttg aggataaaag cagaaagtg aaagatgcaa gcatgcaaga    1500
ctcagataca tttgaaatct atgatcctcg gaatccagtg aataaaagaa ggagggaaga    1560
aagcaaaaag ctgatgagag agaaaaaaga aagaagataa aatgagaata atgataacca    1620
gaacttgctg gaaatgtgcc tacaatggcc ttgtaacagc cattgttccc aacagcatca    1680
cttagggtg tgaaaagaag tatttttgaa cctgttgtct ggttttgaaa acaattatc      1740
ttgttttgca aattgtggaa tgatgtaagc aaatgctttt ggttactggt acatgtgttt    1800
tttcctagct gacctttat attgctaaat ctgaaataaa ataactttcc ttccaaa        1857
```

<210> SEQ ID NO 13
<211> LENGTH: 1537
<212> TYPE: DNA
<213> ORGANISM: Homo sapiens
<220> FEATURE:
<221> NAME/KEY: unsure
<222> LOCATION: 1157..1157
<223> OTHER INFORMATION:

<400> SEQUENCE: 13

```
gccgcgcgcc gatcggtcgt taccgcgagg cgctggtggc cttcaggctg gacggcgcgg      60
```

-continued

```
gtcagccctg gttcgccggc ttctgggtct ttgaacagcc gcgatgtcga tcttccccc      120
caccaaccag atccgcctaa ccaatgtggc cgtggtacgg atgaagcgtg ccgggaagcg      180
cttcgaaatc gcctgctaca aaacaaggt cgtcggctgg cggagcggcg tggaaaaaga      240
cctcgatgaa gttctgcaga cccactcagt gtttgtaaat gtttctaaag gtcaggttgc      300
caaaaaggaa gatctcatca gtgcgtttgg aacagatgac caaactgaaa tctgtaagca      360
gattttgact aaaggagaag ttcaagtatc agataaagaa agacacacac aactggagca      420
gatgtttagg gacattgcaa ctattgtggc agacaaatgt gtgaatcctg aaacaaagag      480
accatacacc gtgatcctta ttgagagagc catgaaggac atccactatt cggtgaaaac      540
caacaagagt acaaaacagc aggctttgga agtgataaag cagttaaaag agaaaatgaa      600
gatagaacgt gctcacatga agcttcggtt catccttcca gtcaatgaag caagaactg      660
aaagaaaagc tcaagccact gatcaaggtc atagaaagtg aagattatgg ccaacagtta      720
gaaatcgtat gtctgattga cccgggctgc ttccgagaaa ttgatgagct aataaaaaag      780
gaaactaaag gcaaaggttc tttggaagta ctcaatctga agatgtaga agaaggagat      840
gagaaatttg aatgacaccc atcaatctct tcacctctaa aacactaaag tgtttccgtt      900
tccgacggca ctgtttcatg tctgtggtct gccaaatact tgcttaaact atttgacatt      960
ttctatcttt gtgttaacag tggacacagc aaggctttcc tacataagta aataatgtg     1020
ggaatgattt ggttttaatt ataaactggg gtctaaatcc taaagcaaaa ttgaaactcc     1080
aagatgcaaa gtccagagtg gcattttgct actctgtctc atgccttgat agctttccaa     1140
aatgaaagtt acttgangca gctcttgtgg gtgaaaagtt atttgtacag tagagtaaga     1200
ttattagggg tatgtctata caacaaaagg ggggtctttt cctaaaaaag aaaacatatg     1260
atgcttcatt tctacttaat ggaacttgtg ttctgagggt cattatggta tcgtaatgta     1320
aagcttggat gatgttcctg attatttgag gaacagatat aggaaaattg tgccggaatt     1380
acctttcatt gaacatgctg ccataaatta ggttattttt ggttaaaaaa taaaagtcaa     1440
ttatttttaa tttttaaagt ttataatata tattaatata ggtaaaattg tatgtaatca     1500
ataaaaccaa ttttatgttt attaaactta aaaaaaa                              1537
```

<210> SEQ ID NO 14
<211> LENGTH: 1211
<212> TYPE: DNA
<213> ORGANISM: Homo sapiens

<400> SEQUENCE: 14

```
accatctttg gaaaggttac agggtatac agtatataac atgttgcgac tgtcagaagt       60
agacattgat gatgacgaaa gaccacataa tccacacaaa ataaaagct gtgaggtttt      120
gtttaatcct tttgatgaca tcattccaag ggaaattaaa aggctgaaaa aagagaaacc      180
agaggaggaa gtaaagaaat tgaaacccaa aggcacaaaa aattttagtt tactttcatt      240
tggagaggaa gctgaggaag aagaggagga agtaaatcga gttagtcaga gcatgaaggg      300
caaaagcaaa agtagtcatg acttgcttaa ggatgatcca catctcagtt ctgttccagt      360
tgtagaaagt gaaaaggtg atgcagcaga tttagttgat gatggagaag atgaaagtgc      420
agagcatgat gaatatattg atggtgatga aagaacctg atgagagaaa gaattgccaa      480
aaaattaaaa aaggacacaa gtgcgaatgt taaatcagct ggagaaggag aagtggaaa      540
gaaatcagtc agccgcagtg aagagctcag aaaagaagca agacaattaa aacgggaact      600
```

-continued

| | |
|---|---|
| cttagcagca gaacaaaaaa aagtagaaaa tgcagcaaaa caagcagaaa aaagaagtga | 660 |
| agaggaagaa gcccctccag atggtgctgt tgccgaatac agaagagaaa agcaaaagta | 720 |
| tgaagctctg aggaagcaac agtcaaagaa gggaacttcc cgggaagatc agacccttgc | 780 |
| actgctgaac cagtttaaat ctaaactcac tcaagcaatt gctgaaacgc tgaaaatga | 840 |
| cattcctgaa acagaagtag aagatgatga aggatggatg tcacatgtac ttcagtttga | 900 |
| ggataaaagc agaaaagtga agatgcaag catgcaagac tcagatacat ttgaaatcta | 960 |
| tgatcctcgg aatccagtga ataaagaag gagggaagaa agcaaaaagc tgatgagaga | 1020 |
| gaaaaaagaa agaagataaa atgagaataa tgataaccag aacttgctgg aaatgtgcct | 1080 |
| acaatggcct tgtaacagcc attgttccca acagcatcac ttaggggtgt gaaaagaagt | 1140 |
| attttttgaac ctgttgtctg gttttgaaaa acaattatct tgttttgcaa attgtggaat | 1200 |
| gatgtaagca a | 1211 |

<210> SEQ ID NO 15
<211> LENGTH: 604
<212> TYPE: DNA
<213> ORGANISM: Homo sapiens

<400> SEQUENCE: 15

| | |
|---|---|
| ccttcggcaa aaattttggg tcccaacttt ttgttccatt ccaaaagggc ttaccttcat | 60 |
| tccctttagc aacagggccc ccaagaagct cccgttcatt caccccttacc ttggccccca | 120 |
| ggttggaccc ccaaaggctc ccttacccca agtgggtgg ttgaataaat cttctcagtt | 180 |
| ccctggctcc caaggcccat tgaagaagat tgtacaaggc gtgcctcaag taccccgagt | 240 |
| ggaaacagaa gcacctgcct cacttcaagc cgtggctgca cccggagcag agcccgttgc | 300 |
| cgagcctggc gctgtcggag ctgtcggtgc agcatgcgga ctcactggag aacatcgacg | 360 |
| agagcgcggt ggccgagagc agagaggagc ggatgggcgg cgcgggcggc gagggcagcg | 420 |
| acgacgacac cttcacctga gcccgcaccg cttcagggac ggagacagga ccgggcgagc | 480 |
| cctggggcgg cggccgctcc tgcactttct cccctccccc acccgcacc tggtggcacc | 540 |
| gggccaggcc caggcgggtg ctgcagcctg gctggacaga gcccaataaa cggatcccac | 600 |
| agcc | 604 |

<210> SEQ ID NO 16
<211> LENGTH: 742
<212> TYPE: DNA
<213> ORGANISM: Homo sapiens

<400> SEQUENCE: 16

| | |
|---|---|
| cccaccaggg ccccctcgat gcagagacag aggtcggtgc tgaccgctgc acgtcgactg | 60 |
| cctaccagga gcagaggccc caggtggagc aagttggcaa agtcgctcct ctctccccag | 120 |
| ggctgccggc aatggggggg cctggccccg gcccctgtga ggaccccgcg ggtgctgggg | 180 |
| gagcaggtgc aggggctcc gagcccctgg tgactgtcac cgtgcagtgc gccttcacag | 240 |
| tggccctgag ggcaggaaga ggagccgacc tgtccagcct gcgggcactg ctgggccaag | 300 |
| ccttccttca ccaggcccag cttgggcaat tcagttacct agcccaggt gaggacgggc | 360 |
| actgggtccc catccccgag gaggagtcgc tgcagagggc ctgcaggac gcagctgcct | 420 |
| gccccagggg gctgcagctg cagtgcaggg gagccgggg tcggccggtc ctttaccagg | 480 |
| tggtggccca gcacagatac tccgcccagg ggccagagga cctgggcttc cgacaggggg | 540 |
| acacggtgga cgtcctgtgt gaagtggacc aggcatggct ggagggccac tgtgacggcc | 600 |

```
gcatcggcat cttccccaag tgcttcgtgg tccccgccgg ccctcggatg tcaggagccc    660
ccggccgcct gccccgatcc cagcagggag atcagcccta atgatgctgt gtccatgatg    720
cttttaataa aacaacccc ca                                              742
```

```
<210> SEQ ID NO 17
<211> LENGTH: 1087
<212> TYPE: DNA
<213> ORGANISM: Homo sapiens

<400> SEQUENCE: 17
```

```
aagatgatgc ctagtaaatt acagaagaac aaacagagac tgcgaaacga tcctctcaat      60
caaaataagg gtaaaccaga cttgaataca acattgccaa ttagacaaac agcatcaatt     120
ttcaaacaac cggtaaccaa agtcacaaat catcctagta ataaagtgaa atcagaccca     180
caacgaatga atgaacagcc acgtcagctt ttctgggaga agaggctaca aggacttagt     240
gcatcagatg taacagaaca aattataaaa accatggaac tacccaaagg tcttcaagga     300
gttggtccag gtagcaatga tgagcccctt ttatctgctg ttgccagtgc tttgcacaca     360
agctctgcgc caatcacagg gcaagtctcc gctgctgtgg aaaagaaccc tgctgtttgg     420
cttaacacat ctcaacccct ctgcaaagct tttattgtca cagatgaaga catcaggaaa     480
caggaagagc gagtacagca agtacgcaag aaattggaag aagcactgat ggcagacatc     540
ttgtcgcgag ctgctgatac agaagagatg gatattgaaa tggacagtgg agatgaagcc     600
taagaatatg atcaggtaac tttcgaccga ctttccccaa gagaaaattc ctagaaattg     660
aacaaaaatg tttccactgg cttttgcctg taagaaaaaa aatgtacccg agcacataga     720 gcttttaat agcactaacc aatgcctttt tagatgtatt tttgatgtat atatctatta     780
ttcaaaaaat catgtttatt ttgagtccta ggacttaaaa ttagtctttt gtaatatcaa     840
gcaggaccct aagatgaagc tgagcttttg atgccaggtg caatttactg gaaatgtagc     900
acttacgtaa aacatttgtt tcccccacag ttttaataag aacagatcag gaattctaaa     960
taaatttccc agttaaagat tattgtgact tcactgtata taaacatatt tttatacttt    1020
attgaaaggg gacacctgta cattcttcca tcgtcactgt aaagacaaat aaatgattat    1080
attcaca                                                               1087
```

```
<210> SEQ ID NO 18
<211> LENGTH: 5878
<212> TYPE: DNA
<213> ORGANISM: Homo sapiens
<220> FEATURE:
<221> NAME/KEY: unsure
<222> LOCATION: 2237..2237
<223> OTHER INFORMATION:
<221> NAME/KEY: unsure
<222> LOCATION: 2260..2260
<223> OTHER INFORMATION:
<221> NAME/KEY: unsure
<222> LOCATION: 2305..2305
<223> OTHER INFORMATION:
<221> NAME/KEY: unsure
<222> LOCATION: 2315..2315
<223> OTHER INFORMATION:
<221> NAME/KEY: unsure
<222> LOCATION: 2355..2355
<223> OTHER INFORMATION:
<221> NAME/KEY: unsure
<222> LOCATION: 2420..2420
<223> OTHER INFORMATION:
<221> NAME/KEY: unsure
<222> LOCATION: 2421..2421
```

```
<223> OTHER INFORMATION:
<221> NAME/KEY: unsure
<222> LOCATION: 2423..2423
<223> OTHER INFORMATION:
<221> NAME/KEY: unsure
<222> LOCATION: 2490..2490
<223> OTHER INFORMATION:
<221> NAME/KEY: unsure
<222> LOCATION: 2523..2523
<223> OTHER INFORMATION:

<400> SEQUENCE: 18
```

| | | | | |
|---|---|---|---|---|
| aagagtaaaa | gctactcttt | cagagagaaa | aataggagat | tcatgtgaca aagatttgcc | 60 |
| tctgaaattt | tgtgagttcc | cacagaagac | tataatgcct | ggatttaaaa caactgtata | 120 |
| tgtttctcat | ataaatgacc | tttcagactt | ttatgttcaa | ctaatagaag atgaagctga | 180 |
| aattagtcat | ctttcagaga | gattaaacag | tgttaaaaca | aggcccgaat attatgtagg | 240 |
| tccacctttg | caaagaggag | atatgatatg | tgctgttttc | ccagaagata atttatggta | 300 |
| tcgtgctgtg | atcaaggagc | aacaacccaa | tgaccttctc | tctgtgcagt ttatagatta | 360 |
| tggcaatgtt | tctgtggttc | atactaacaa | aataggtagg | cttgaccttg ttaatgcaat | 420 |
| attgccgggg | ttgtgcattc | attgctcctt | gcagggattt | gaggttcctg acaataaaaa | 480 |
| ttctaagaaa | atgatgcatt | acttttccca | acggaccagc | gaggctgcaa taagatgtga | 540 |
| atttgttaaa | tttcaagaca | gatgggaagt | tattcttgct | gatgaacatg ggatcatagc | 600 |
| agatgatatg | attagcaggt | atgctctcag | tgaaaaatct | caagtagaac tttctaccca | 660 |
| agtaattaaa | agtgccagtt | caaagtctgt | taacaaatca | gacattgaca cttcagtatt | 720 |
| tcttaactgg | tataatccag | aaaaaaaaat | gataagagct | tatgccactg tgatagatgg | 780 |
| acctgagtac | ttttggtgtc | agtttgctga | tacggagaaa | cttcagtgtt tagaagtaga | 840 |
| agtacagact | gctggagaac | aggtagcaga | caggagaaat | tgtatcccat gtccttatat | 900 |
| tggagatcct | tgtatagtaa | gatacagaga | agatggacat | tattataggg cacttatcac | 960 |
| taatatttgt | gaagattatc | ttgtatctgt | caggcttgtg | gactttggaa acattgaaga | 1020 |
| ctgtgtggac | ccaaaagcac | tctgggccat | tccttctgaa | cttctgtcgg ttcccatgca | 1080 |
| agccttccca | tgttgcctct | cagggtttaa | catttcagaa | ggattatgtt ctcaagaggg | 1140 |
| aaatgactat | ttctatgaaa | taataacaga | agatgtgttg | gaaataacaa tactagaaat | 1200 |
| cagaagggat | gtttgtgata | tccctttagc | aattgttgac | ttgaaaagca aggtaaaag | 1260 |
| tattaatgag | aaaatggaga | aatattctaa | gactggtatt | aaaagtgctc ttccctatga | 1320 |
| aaatattgac | tcagagataa | agcagactct | tgggtcctac | aatcttgatg taggacttaa | 1380 |
| gaaattaagt | aataaagctg | tacaaaataa | aatatatatg | gaacaacaga cagatgagct | 1440 |
| tgctgaaata | actgaaaaag | atgtaaacat | tattggaacc | aaaccaagta acttccgtga | 1500 |
| ccctaaaact | gataacattt | gtgaagggtt | tgaaaacccc | tgcaaagata aaattgatac | 1560 |
| tgaggaactg | gaaggtgaat | tagagtgcca | tctggttgac | aaagcagagt ttgatgataa | 1620 |
| ataccctgatt | acaggattta | acacattact | accacatgct | aatgaaacaa aggagatact | 1680 |
| agaactgaat | tcacttgagg | tgccgctttc | tcctgatgat | gaatcaaaag aattcttaga | 1740 |
| actggaatct | attgagttac | agaattctct | ggtggtggat | gaagaaaaag gggagctaag | 1800 |
| cccggtgcca | ccgaatgtgc | cactctccca | agagtgtgtc | acaaaaggcg ccatggagct | 1860 |
| atttacactg | cagcttcctc | tcagctgtga | agctgagaaa | cagccagaac tagaactacc | 1920 |
| tacagcccag | ctgcctttag | atgacaagat | ggatcctttg | tctttaggag ttagtcagaa | 1980 |

-continued

```
agcacaggaa tccatgtgta ctgaggacat gagaaagtca agttgtgtag aatcttttga    2040
tgaccagcgc aggatgtcat tgcatctaca tggagcagat tgtgatccta aaacacagaa    2100
tgaaatgaat atatgtgaag aagaatttgt agagtataaa aacagggatg ccatttcggc    2160
attgatgcct tttctctga ggaagaaagc agtgatggaa gcaagcacaa taatggttta    2220
ccagatcata tttcagntca attacagaac acctacactn tgaaagcctt tactgttgga    2280
tctaaatgtg ttgtgtggtc aagtntaaga aacanatggt ctaaatgtga gattttagaa    2340
acagctgaag aaggnacaag ggttttgaac ctttcaaatg gtatggagga gatagtgaac    2400
cctgagaatg tctggaatgn nanacccaaa ttggataaga gtccacctga gaaaggggt    2460 ttggaggtga tggagattta accgtggatn tatagctgtg ccaatcagt cagaagctgc    2520 ccntgaacaa gtggcatctt acgcagacca acagagtatt tgagaaaatc gcagaccgag    2580
acccgaggcg gaggcggacc gcgagccggc catgtcggtg gtggggttgg acgtgggctc    2640
gcagagctgc tacatcgcgg tagcccgggc cgggggcatc gagaccatcg ccaatgagtt    2700
cagcgaccgg tgcacccgt cagtcatatc atttggatca aaaatagaa caatcggagt    2760 tgcagccaaa aatcagcaaa tcactcatgc aaacaatacg gtgtctaact tcaaaagatt    2820
tcatggccga gcattcaatg accccttcat tcaaaaggag aaggaaaact tgagttacga    2880
tttggttcca ttgaaaaatg gtggagttgg aataaaggta atgtacatgg gtgaagaaca    2940
tctatttagt gtggagcaga taacagccat gttgttgact aagctgaagg aaactgctga    3000
aaacagcctc aagaaaccag taacagattg tgttatttca gtcccctcct tctttacaga    3060
tgctgagagg cgatctgtgt tagatgctgc acagattgtt ggcctaaaact gtttaagact    3120 tatgaatgac atgacagctg ttgctttgaa ttacggaatt tataagcagg atctcccaag    3180
cctggatgag aaacctcgga tagtggtttt tgttgatatg ggacattcag cttttcaagt    3240
gtctgcttgt gctttaaca agggaaaatt gaaggtactg ggaacagctt ttgatccttt    3300
cttaggagga aaaaacttcg atgaaaagtt agtggaacat ttttgtgcag aatttaaaac    3360
taagtacaag ttggatgcaa aatccaaaat acgagcactc ctacgtctgt atcaggaatg    3420
tgaaaaactg aaaaagctaa tgagctctaa cagcacagac cttccactga atatcgaatg    3480
ctttatgaat gataaagatg tttccggaaa gatgaacagg tcacaatttg aagaactctg    3540
tgctgaactt ctgcaaaaga tagaagtacc cctttattca ctgttggaac aaactcatct    3600
caaagtagaa gatgtgagtg cagttgagat tgttggaggc gctacacgaa ttccagctgt    3660
gaaggaaaga attgccaaat tctttggaaa agatattagc acaacactca atgcagatga    3720
agcagtagcc agaggatgtg cattacagtg tgcaatactt tccccggcat ttaaagttag    3780
agaattttcc gtcacagatg cagttccttt tccaatatct ctgatctgga accatgattc    3840
agaagatact gaaggtgttc atgaagtctt tagtcgaaac catgctgctc ctttctccaa    3900
agttctcacc tttctgagaa ggggggcttt tgagctagaa gctttctatt ctgatcccca    3960
aggagttcca tatccagaag caaaatagg ccgctttgta gttcagaatg tttctgcaca    4020
gaaagatgga gaaaaatcta gagtaaaagt caaagtgcga gtcaacaccc atggcatttt    4080
caccatctct acggcatcta tggtggagaa agtcccaact gaggagaatg aaatgtcttc    4140
tgaagctgac atggagtgtc tgaatcagag accaccagaa aacccagaca ctgataaaaa    4200
tgtccagcaa gacaacagtg aagctggaac acagccccag gtacaaactg atgctcaaca    4260
aacctcacag tctcccccctt cacctgaact tacctcagaa gaaaacaaaa tcccagatgc    4320
tgacaaagca aatgaaaaaa aagttgacca gcctccagaa gctaaaaagc ccaaaataaa    4380
```

```
ggtggtgaat gttgagctgc ctattgaagc caacttggtc tggcagttag ggaaagacct    4440
tcttaacatg tatattgaga cagagggtaa gatgataatg caagataaat tggaaaaaga    4500
aaggaatgat gctaaaaatg cagttgagga atatgtgtat gagttcagag acaagctgtg    4560
tggaccatat gaaaaattta tatgtgagca ggatcatcaa aattttttga gactcctcac    4620
agaaactgaa gactggctgt atgaagaagg agaggaccaa gctaaacaag catatgttga    4680
caagttggaa gaattaatga aaattggcac tccagttaaa gttcggtttc aggaagctga    4740
agaacggcca aaaatgtttg aagaactagg acagaggctg cagcattatg ccaagatagc    4800
agctgacttc agaaataagg atgagaaata caaccatatt gatgagtctg aaatgaaaaa    4860
agtggagaag tctgttaatg aagtgatgga atggatgaat aatgtcatga atgctcaggc    4920
taaaaagagt cttgatcagg atccagttgt acgtgctcag gaaattaaaa caaaaatcaa    4980
ggaattgaac aacacatgtg aacccgttgt aacacaaccg aaaccaaaaa ttgaatcacc    5040
caaactggaa agaactccaa atggcccaaa tattgataaa aaggaagaag atttagaaga    5100
caaaaacaat tttggtgctg aacctccaca tcagaatggt gaatgttacc ctaatgagaa    5160
aaattctgtt aatatggact tggactagat aaccttaaat tggcctattc cttcaattaa    5220
taaaatattt ttgccatagt atgtgactct acataacata ctgaaactat ttatatttttc    5280 ttttttaagg atatttagaa attttgtgta ttatatggaa aagaaaaaa agcttaagtc    5340 tgtagtcttt atgatcctaa aagggaaaat tgccttggta actttcagat tcctgtggaa    5400
ttgtgaattc atactaagct ttctgtgcag tctccaccatt tgcatcactg aggatgaaac    5460
tgacttttgt ctttttggaga aaaaaaactg tactgcttgt tcaagagggc tgtgattaaa    5520
atctttaagc atttgttcct gccaaggtag ttttcttgca ttttgctctc cattcagcat    5580
gtgtgtgggt gtggatgttt ataaacaaga ctaagtctga cttcataagg gctttctaaa    5640
accatttctg tccaagagaa aatgactttt tgctttgata ttaaaaattc aatgagtaaa    5700
acaaaagcta gtcaaatgtg ttagcagcat gcagaacaaa aactttaaac tttctctctc    5760
actatacagt atattgtcat gtgaaagtgt ggaatggaag aaatgtcgat cctgttgtaa    5820
ctgattgtga acacttttat gagctttaaa ataaagttca tcttatggtg tcatttct      5878
```

<210> SEQ ID NO 19
<211> LENGTH: 2077
<212> TYPE: DNA
<213> ORGANISM: Homo sapiens

<400> SEQUENCE: 19

```
ctgttgattt tttggagaaa tatgggagaa acagtggaat atttttatga cattttttagg     60 aaatcacctg gcttggttgg tagtcccaca ctgactttcc ttatgataat tctacagatg    120
gaggtgactc gagcagtgat gaggataaag aataacatga aactcctgtg aagtagaac    180 tcatgactca ggttgaccaa gaggatatca ctcttcagag tggcagagat gaactaaatg    240
aggagctcat tcaggaagaa agctctgaag acgaaggaga atatgaagag gttagaaaag    300
atcaggattc tgttggtgaa atgaaggatg aaggggaaga gacttaaatt atcctgatac    360
taccattgac ttgtctcacc ttcaaccca aggtccatc cagaaattgg cttcaaaaga    420
ggaatcttct aattctagtg acagtaaatc acagagccgg agacatttgt cagccaagga    480
aagaagggaa atgaaaaaga aaaaacttcc aagtgactca ggagattag aagcgttaga    540 gggaaaggat aaagaaaaag aaagtactgt acacattgaa actcatcaga acacaagcaa    600
```

-continued

| | | |
|---|---|---|
| aaatgttgcg gctgtgcagc caatgaaacg aggacaaaag agtaaaatga aaaaaatgaa | 660 |
| agaaaaatac aaagaccagg atgaagaaga ccgtgaactt atcatgaagt tgctggggtc | 720 |
| tgcaggttca aacaaagaag aaaaagggaa gaaggggaag aaaggaaaaa caaaggacga | 780 |
| acctgtgaag aaacagcccc agaaacctag aggtggacag agggtctctg acaacattaa | 840 |
| gaaagaaact ccgttccttg aggttataac tcatgagtta caagactttg ctgtagatga | 900 |
| tccacatgat gacaaggaag agcaagatct ggatcaacag ggaaatgagg aaaacctatt | 960 |
| tgattctttg acaggccagc cacatcctga agatgtacta ctgttttgcca ttccaatatg | 1020 |
| tgccccttac accaccatga caaactacaa atataaagtg aaacttactc ctggagtgca | 1080 |
| gaaaaaggga aaagctgcaa aaacagcctt gaatagtttc atgcattcca agaagcaac | 1140 |
| agcaagagaa aaagacttat tccgcagcgt aaaggacaca gatttatcaa gaaacattcc | 1200 |
| tggcaaagtg aaaagtgtct gcacccaatc ttctgaacgt aaaaaggaaa tagctgaaat | 1260 |
| gaaattctaa aatatttgag aagagccaat tttatagcct tttggaagtt caaagatgaa | 1320 |
| agcaccatgt atcaggattt ccgcattata aaaatgaact aaacattgcc ttgctatatt | 1380 |
| caccaaaagg acttaattct tgttttttc ccagttttat atagaggaaa cactgtctat | 1440 |
| gataggattt ccaaaagtat ttgtggacag ttaaatgcta attatataca tctgtagtta | 1500 |
| ttctacattt tcttgaaatt tgggaggtta ataccaagta ttcatttcat gatgtaaaga | 1560 |
| aactgaacag tgaagtggct tgattgctta aactattgac ttggtaagtc tactgtatat | 1620 |
| aacatctaat atatatatta caggccaaat gaactaaaca ttgccttgct atattcacca | 1680 |
| aaaggactta attcttgttt ttttcccagt tttatataga ggaaacacta tgataggatt | 1740 |
| tcctaaagta tttgtggaca gttaaatgct aattatatac atctgtagtt attctacatt | 1800 |
| ttcttgaaat ttgagaggtt aataccaagt attcatttca tgatgtaaag aaactgaaca | 1860 |
| gtgaagtggc ttgattgctt aaactattga cttggtaagt ctactgtata aacatctaa | 1920 |
| tatatatata ttataggcca gctacaaggg gtttaaatat ttaggattgt gtcttgaaaa | 1980 |
| ctaagtattg gagtggattt tcttctgctt tcattgatac ttgtcagaaa aaatattag | 2040 |
| accaaaatgt aaaatataag taataattct catgaaa | 2077 |

<210> SEQ ID NO 20
<211> LENGTH: 3309
<212> TYPE: DNA
<213> ORGANISM: Homo sapiens

<400> SEQUENCE: 20

| | | |
|---|---|---|
| cgcagaccga gacccgaggc ggaggcggac cgcgagccgg ccatgtcggt ggtggggttg | 60 |
| gacgtgggct cgcagagctg ctacatcgcg gtagcccggg ccgggggcat cgagaccatc | 120 |
| gccaatgagt tcagcgaccg gtgcacccg tcagtcatat catttggatc aaaaaataga | 180 |
| acaatcggag ttgcagccaa aaatcagcaa atcactcatg caaacaatac ggtgtctaac | 240 |
| ttcaaaagat ttcatggccg agcattcaat gacccctca ttcaaaagga aaggaaaac | 300 |
| ttgagttacg atttggttcc attgaaaaat ggtggagttg aataaaggt aatgtacatg | 360 |
| ggtgaagaac atctatttag tgtggagcag ataacagcca tgttgttgac taagctgaag | 420 |
| gaaactgctg aaaacagcct caagaaacca gtaacagatt gtgttatttc agtcccctcc | 480 |
| ttctttacag atgctgagag gcgatctgtt ttagatgctg cacagattgt tggcctaaac | 540 |
| tgtttaagac ttatgaatga catgacagct gttgctttga attacggaat tttataagcag | 600 |
| gatctcccaa gcctggatga gaaacctcgg atagtggttt tgttgatat gggacattca | 660 |

-continued

```
gcttttcaag tgtctgcttg tgcttttaac aagggaaaat tgaaggtact gggaacagct      720
tttgatcctt tcttaggagg aaaaaacttc gatgaaagt tagtggaaca tttttgtgca       780
gaatttaaaa ctaagtacaa gttggatgca aaatccaaaa tacgagcact cctacgtctg      840
tatcaggaat gtgaaaaact gaaaaagcta atgagctcta acagcacaga ccttccactg      900
aatatcgaat gctttatgaa tgataaagat gtttccggaa agatgaacag gtcacaattt     960
gaagaactct gtgctgaact tctgcaaaag atagaagtac ccctttattc actgttggaa      1020
caaactcatc tcaaagtaga gatgtgagt gcagttgaga ttgttggagg cgctacacga       1080
attccagctg tgaaggaaag aattgccaaa ttctttggaa agatattag cacaacactc       1140 aatgcagatg aagcagtagc cagaggatgt gcattacagt gtgcaatact tccccggca      1200 tttaaagtta gagaattttc cgtcacagat gcagttcctt ttccaatatc tctgatctgg      1260
aaccatgatt cagaagatac tgaaggtgtt catgaagtct ttagtcgaaa ccatgctgct      1320
cctttctcca aagttctcac ctttctgaga agggggcctt tgagctaga agctttctat       1380 tctgatcccc aaggagttcc atatccagaa gcaaaaatag gccgctttgt agttcagaat      1440
gtttctgcac agaaagatgg agaaaaatct agagtaaaag tcaaagtgcg agtcaacacc      1500
catggcattt tcaccatctc tacggcatct atggtggaga agtcccaac tgaggagaat       1560 gaaatgtctt ctgaagctga catggagtgt ctgaatcaga gaccaccaga aacccagac       1620 actgataaaa atgtccagca agacaacagt gaagctggaa cacagcccca ggtacaaact      1680
gatgctcaac aaacctcaca gtctccccct tcacctgaac ttacctcaga gaaaacaaa      1740 atcccagatg ctgacaaagc aaatgaaaaa aagttgacc agcctccaga agctaaaaag      1800
cccaaaataa aggtggtgaa tgttgagctg cctattgaag ccaacttggt ctggcagtta      1860
gggaaagacc ttcttaacat gtatattgag acagagggta agatgataat gcaagataaa      1920
ttggaaaaag aaaggaatga tgctaaaaat gcagttgagg aatatgtgta tgagttcaga      1980
gacaagctgt gtggaccata tgaaaaattt atatgtgagc aggatcatca aaattttttg     2040
agactcctca cagaaactga agactggctg tatgaagaag gagaggacca agctaaacaa      2100
gcatatgttg acaagttgga agaattaatg aaaattggca ctccagttaa agttcggttt      2160
caggaagctg aagaacggcc aaaaatgttt gaagaactag acagaggct gcagcattat      2220 gccaagatag cagctgactt cagaaataag gatgagaaat acaaccatat tgatgagtct      2280
gaaatgaaaa agtggagaa gtctgttaat gaagtgatgg aatggatgaa taatgtcatg      2340
aatgctcagg ctaaaagag tcttgatcag gatccagttg tacgtgctca ggaaattaaa      2400
acaaaaatca aggaattgaa caacacatgt gaacccgttg taacacaacc gaaaccaaaa      2460
attgaatcac ccaaactgga agaactcca aatggcccaa atattgataa aaaggaagaa      2520
gatttagaag acaaaaacaa ttttggtgct gaacctccac atcagaatgg tgaatgttac      2580
cctaatgaga aaaattctgt taatatggac ttggactaga taaccttaaa ttggcctatt      2640
ccttcaatta ataaaatatt tttgccatag tatgtgactc tacataacat actgaaacta      2700
tttatatttt cttttttaag gatatttaga aattttgtgt attatatgga aaagaaaaa      2760 aagcttaagt ctgtagtctt tatgatccta aaagggaaaa ttgccttggt aactttcaga      2820
ttcctgtgga attgtgaatt catactaagc tttctgtgca gtctcaccat ttgcatcact      2880
gaggatgaaa ctgacttttg tcttttggag aaaaaaaact gtactgcttg ttcaagaggg      2940
ctgtgattaa aatctttaag catttgttcc tgccaaggta gttttcttgc attttgctct      3000
```

-continued

| | |
|---|---|
| ccattcagca tgtgtgtggg tgtggatgtt tataaacaag actaagtctg acttcataag | 3060 |
| ggctttctaa aaccatttct gtccaagaga aaatgacttt ttgctttgat attaaaaatt | 3120 |
| caatgagtaa aacaaaagct agtcaaatgt gttagcagca tgcagaacaa aaactttaaa | 3180 |
| ctttctctct cactatacag tatattgtca tgtgaaagtg tggaatggaa gaaatgtcga | 3240 |
| tcctgttgta actgattgtg aacactttta tgagctttaa aataaagttc atcttatggt | 3300 |
| gtcatttct | 3309 |

<210> SEQ ID NO 21
<211> LENGTH: 2918
<212> TYPE: DNA
<213> ORGANISM: Homo sapiens

<400> SEQUENCE: 21

| | |
|---|---|
| ataactggag ctcgcgcgcc tgcaggtcga cactagtgga tccaaagaat tcggcacgag | 60 |
| gtgacgacaa cagggacaag gactccgaga agaccaagag gtggtccaag cccaggaagc | 120 |
| gctccctgat ggagatggag gggaaggagg atgccccttta aggtgctgaa gtgcatgtac | 180 |
| tgtggacact cctttgagtc cttgcaggac ctcagcgtcc acatgatcaa aaccaagcat | 240 |
| taccagaaag tgcctctgaa ggagccagtg ccagccatca ccaaactggt cccctccacc | 300 |
| aaaaagcggg cgcttcagga cctggcgccc ccctgctccc ctgagccagc aggaatggcc | 360 |
| gcagaggtgg ccctgagtga gtcagccaag gatcagaaag cagcgaaccc gtacgtcacg | 420 |
| cccaataacc gctatggcta ccagaatggc gccagctaca cctggcagtt tgaggcccgc | 480 |
| aaggcgcaga tcctcaagtg catggagtgt ggcagctccc acgacacgct gcagcagctc | 540 |
| accgcccaca tgatggtcac cgggcacttc ctgaaagtga ccacctcggc ttctaagaag | 600 |
| ggcaagcagt tggtgctgga ccctgtggtg gaagagaaga tccagtccat cccactaccg | 660 |
| cccaccaccc acacgcggct gccggcctcc agcatcaaaa agcagcccga ctctcccgcg | 720 |
| gggtccacga cttctgaaga aaagaaagag ccagagaagg agaagccgcc tgtggctggc | 780 |
| gacgcggaga agatcaagga ggagagtgag gacagcttgg agaaatttga gcccagcacc | 840 |
| ctgtacccgt acctgcgtga ggaggacctg gacgacagcc caagggagg ctggacatt | 900 |
| ctcaagtccc tggagaatac cgtctccacg gccattagca aagctcagaa tggtgcgccc | 960 |
| tcatggggtg gctaccccag catccatgca gcctaccagc tcccgggcac cgtgaagcca | 1020 |
| ctgccggcgg ccgtgcagag cgtgcaggtg cagccgtcct atgctggcgg cgtgaagtcg | 1080 |
| ctgtcttccg ccgagcacaa cgccctcctg cactcccccag ggagcctcac gccccaccg | 1140 |
| cacaagagca acgtgtctgc catggaggag ctggtggaga aggtcacggg caaggtcaac | 1200 |
| atcaagaagg aggagagacc ccctgagaag gagaagagct ccctggccaa ggctgcgtcc | 1260 |
| cccatagcaa aagagaataa agattcccg aaaacggagg aagtcagcgg caaaccacag | 1320 |
| aagaagggcc ctgaggccga gacttgggaa gccaaaaagg agggaccgct ggacgttcac | 1380 |
| accccaaatg gcacagagcc tctcaaagca aaggtcacca acggctgtaa caacctgggg | 1440 |
| atcatcatgg accactcacc ggagccttcc ttcatcaacc cgctgagcgc tttgcagtcc | 1500 |
| atcatgaaca cccacctggg caaggtgtcc aagcccgtga gtccctcgct ggaccccgctg | 1560 |
| gcgatgctgt acaagatcag caacagcatg ctggacaagc cggtgtaccc cgccacccct | 1620 |
| gtgaagcagg ccgatgccat cgaccgctac tattatgaaa acagcgacca gcccattgac | 1680 |
| ttaaccaagt ccaagaacaa gccgctggtg tccagcgtgg ctgattcggt ggcatcacct | 1740 |
| ctgcgggaga gcgcactcat ggacatctcc gacatggtga aaaacctcac aggccgcctg | 1800 |

-continued

```
acgcccaagt cctccacgcc ctccacagtt tcagagaagt ccgatgctga tggcagcagc    1860
tttgaggagg cgttggacga gctgtcaccg gtccacaaga ggaagggccg gcagtccaac    1920
tggaacccgc agcaccttct catcctgcag gcccagttcg cctcgagctt gcgggagacc    1980
acagaaggca agtacatcat gtcggacttg ggccgcagg agagggtgca catctcgaag    2040
tttactgggc tctccatgac caccatcagc cactggctgg ccaatgtgaa gtaccagttg    2100
aggaggacag ggggaacgaa attcctaaag aacctggaca cagggcatcc tgttttcttt    2160
tgcaacgatt gtgcctctca gttcagaact gcttctacat acataagtca tttggagaca    2220
cacttgggct tcagcctgaa ggatctctcc aagctgccac tcaatcagat tcaagaacag    2280
cagaatgttt cgaaagtcct caccaacaaa actctgggcc cactggggc caccgaggaa    2340 gacttgggct ccacattcca atgtaagctc tgcaaccgga cttttgcgaa gcaagcacgc    2400
agtcaaactg caccttagta agacccacgg caagtctccc gaggaccacc tgatctatgt    2460
gactgagttg gagaaacagt agcgtccagg tatgcaagag accgcggaac attgcactaa    2520
acgtcgtcga gctgcactag gcatggcctg agcctctgaa atcagtcttt cctttgttgc    2580
tggcccgcct ctctggacct tggttttcct acacatattt tgtatattta tatgctttct    2640
gtccgatctg tgcatgttat ttttcttttt ccgtgagtca aagtctgacc tttattttca    2700
acatctgttt ttggtgttaa gctatctttt gtaggaaata gtggggcaca ctactcagag    2760
acattattta gcagtaaaga aagacacaaa taacaatgat aaaaagacat cctaaaatgg    2820
tgaagttgcc atgacaataa aggtcataga acctggtagt gtcaaattta acccttgag    2880 gactgtaatt gcatttctgt gcctttcact tgaaaaaa                           2918
```

<210> SEQ ID NO 22
<211> LENGTH: 1898
<212> TYPE: DNA
<213> ORGANISM: Homo sapiens
<220> FEATURE:
<221> NAME/KEY: unsure
<222> LOCATION: 191..191
<223> OTHER INFORMATION:
<221> NAME/KEY: unsure
<222> LOCATION: 273..273
<223> OTHER INFORMATION:
<221> NAME/KEY: unsure
<222> LOCATION: 315..315
<223> OTHER INFORMATION:
<221> NAME/KEY: unsure
<222> LOCATION: 587..587
<223> OTHER INFORMATION:
<221> NAME/KEY: unsure
<222> LOCATION: 594..594
<223> OTHER INFORMATION:
<221> NAME/KEY: unsure
<222> LOCATION: 609..609
<223> OTHER INFORMATION:
<221> NAME/KEY: unsure
<222> LOCATION: 618..618
<223> OTHER INFORMATION:
<221> NAME/KEY: unsure
<222> LOCATION: 630..630
<223> OTHER INFORMATION:
<221> NAME/KEY: unsure
<222> LOCATION: 655..655
<223> OTHER INFORMATION:
<221> NAME/KEY: unsure
<222> LOCATION: 656..656
<223> OTHER INFORMATION:
<221> NAME/KEY: unsure
<222> LOCATION: 693..693
<223> OTHER INFORMATION:
<221> NAME/KEY: unsure -continued

```
<222> LOCATION: 719..719
<223> OTHER INFORMATION:
<221> NAME/KEY: unsure
<222> LOCATION: 1220..1220
<223> OTHER INFORMATION:
<221> NAME/KEY: unsure
<222> LOCATION: 1294..1294
<223> OTHER INFORMATION:
<221> NAME/KEY: unsure
<222> LOCATION: 1366..1366
<223> OTHER INFORMATION:
<221> NAME/KEY: unsure
<222> LOCATION: 1375..1375
<223> OTHER INFORMATION:
<221> NAME/KEY: unsure
<222> LOCATION: 1381..1381
<223> OTHER INFORMATION:
<221> NAME/KEY: unsure
<222> LOCATION: 1391..1391
<223> OTHER INFORMATION:
<221> NAME/KEY: unsure
<222> LOCATION: 1468..1468
<223> OTHER INFORMATION:
<221> NAME/KEY: unsure
<222> LOCATION: 1471..1471
<223> OTHER INFORMATION:
<221> NAME/KEY: unsure
<222> LOCATION: 1487..1487
<223> OTHER INFORMATION:
<221> NAME/KEY: unsure
<222> LOCATION: 1497..1497
<223> OTHER INFORMATION:
<221> NAME/KEY: unsure
<222> LOCATION: 1520..1520
<223> OTHER INFORMATION:
<221> NAME/KEY: unsure
<222> LOCATION: 1543..1543
<223> OTHER INFORMATION:
<221> NAME/KEY: unsure
<222> LOCATION: 1551..1551
<223> OTHER INFORMATION:
<221> NAME/KEY: unsure
<222> LOCATION: 1557..1557
<223> OTHER INFORMATION:
<221> NAME/KEY: unsure
<222> LOCATION: 1560..1560
<223> OTHER INFORMATION:
<221> NAME/KEY: unsure
<222> LOCATION: 1590..1590
<223> OTHER INFORMATION:
<221> NAME/KEY: unsure
<222> LOCATION: 1612..1612
<223> OTHER INFORMATION:
<221> NAME/KEY: unsure
<222> LOCATION: 1632..1632
<223> OTHER INFORMATION:
<221> NAME/KEY: unsure
<222> LOCATION: 1634..1634
<223> OTHER INFORMATION:
<221> NAME/KEY: unsure
<222> LOCATION: 1638..1638
<223> OTHER INFORMATION:
<221> NAME/KEY: unsure
<222> LOCATION: 1705..1705
<223> OTHER INFORMATION:
<221> NAME/KEY: unsure
<222> LOCATION: 1716..1716
<223> OTHER INFORMATION:
<221> NAME/KEY: unsure
<222> LOCATION: 1721..1721
<223> OTHER INFORMATION:
<221> NAME/KEY: unsure
<222> LOCATION: 1738..1738
<223> OTHER INFORMATION:
<221> NAME/KEY: unsure
<222> LOCATION: 1755..1755
<223> OTHER INFORMATION:
<221> NAME/KEY: unsure
<222> LOCATION: 1765..1765
```

```
<223> OTHER INFORMATION:
<221> NAME/KEY: unsure
<222> LOCATION: 1778..1778
<223> OTHER INFORMATION:
<221> NAME/KEY: unsure
<222> LOCATION: 1780..1780
<223> OTHER INFORMATION:
<221> NAME/KEY: unsure
<222> LOCATION: 1781..1781
<223> OTHER INFORMATION:
<221> NAME/KEY: unsure
<222> LOCATION: 1807..1807
<223> OTHER INFORMATION:
<221> NAME/KEY: unsure
<222> LOCATION: 1811..1811
<223> OTHER INFORMATION:
<221> NAME/KEY: unsure
<222> LOCATION: 1818..1818
<223> OTHER INFORMATION:
<221> NAME/KEY: unsure
<222> LOCATION: 1821..1821
<223> OTHER INFORMATION:
<221> NAME/KEY: unsure
<222> LOCATION: 1823..1823
<223> OTHER INFORMATION:
<221> NAME/KEY: unsure
<222> LOCATION: 1824..1824
<223> OTHER INFORMATION:
<221> NAME/KEY: unsure
<222> LOCATION: 1829..1829
<223> OTHER INFORMATION:
<221> NAME/KEY: unsure
<222> LOCATION: 1839..1839
<223> OTHER INFORMATION:
<221> NAME/KEY: unsure
<222> LOCATION: 1871..1871
<223> OTHER INFORMATION:
<221> NAME/KEY: unsure
<222> LOCATION: 1884..1884
<223> OTHER INFORMATION:

<400> SEQUENCE: 22
ccgccttggg tcagcctgct ccctgcttc ctgccgcagt gggggccgtc agcctggcca      60
cctcccagct cccaagccca cccctggggc ccaccgtccc cccacagcca ccctcggccc    120
tggagtcgga tggggaaggg ccgcccccca gggtgggctt tgtggacagc accatcaaga    180
gcctggacga naagctgcgg actctgctct accaggagca cgtgcccacc tcctcagcct    240
cagctgggac ccctgtggag gtgggcgaca ganacttcac cctggagccc ctgagagggg    300
accagccccg ctcanaggtc tgcgggggg acctggccct gccccagtg cctaaggagg     360 cggtctcagg gcgtgtccag ctgccccagc ccttggtgga aagtcagaa ctggccccca    420 ctcgagggc cgtgatggag cagggcacgt cctcgtcaat gacagagtcg tctcccagga    480
gtatgctagg ctatgacaga gatggaaggc aggtggcctc agactccat gtggtcccca    540 gcgtccccca ggatgtacct gcttttgtga gacctgcacg tgtggancc acanacaggg    600 atggtggana agctgganaa agctcggcan agccccgcc gagtgacatg ggcanngtgg    660
ggggccaggc tagccacccc cagacactcg gcnctcgagc tttggggtcc cctcggaanc    720
gtccagatca ccaggatgtc agctcaccag ccaagactgt gggccgtttc tcggtggtca    780
gcactcagga cgagtggacc ctggcctccc cccacagcct gagatactct gccccacccg    840
acgtctacct ggacgaggcc ccctccagcc ccgacgtgaa gctggcagtg cggcgggcgc    900
agacggcctc ctccatcgag gtcggcgtgg gcgagcccgt gtccagcgac tctggggacg    960
agggccctcg ggcgagaccc ccggtgcaga agcaggcgtc cctgcccgtg agtggcagcg   1020
tggctggcga cttcgtgaag aaggccaccg cttcctgcag aggccttctc gggccggctt   1080
```

```
cgctgggccc cgagacaccc agcagggtgg gcatgaaggt ccccacgatc agcgtgacct    1140
ccttccattc ccagtcgtcc tacatcagca gcgacaatga ttcggagctc gaggatgctg    1200
acataaagaa ggagctgcan agtctgcggg agaagcacct gaaggagatc tcggagctgc    1260
agagccagca gaagcaggag atcgaagctc tgtnccgccg cctgggcaag ccactgcccc    1320
ccaacgtggg cttcttccac acggcacccc ccactggccg ccgganaaaa accancaaga    1380
ncaagctgaa ngcaggcaag ctgctaaatc ccctggtgcg gcagctcaag gtcgtggcct    1440
ccaacacagg tcacttggct gactccanca naagccctcc cgctaangac ctgcccnagc    1500
cagtgtgggg ctcactgcan acaacacggg cctgaacggg aangcagtgc anaccancan    1560
ccctgctccg tccggggctc cctgtcttcn gacatctgct ccggcttacc antgatggaa    1620
gcggaacgcg tngncaangg tcctccacca acaacctggc ccaggcctga accaagcccc    1680
acccgccctg cacgtccaag cgcangtgaa caacancaac nacaagaaag gttcttcncc    1740
gacgaactgc acaanctggt ggacnaatgg acaacaanan ngtgggggc gcgcactgaa    1800 acccacnctc naccccctnaa ncnnaaccnc aacttccana cattgaggcc cgcaggtggg    1860
ctgccctggc naagcccggc tttnaccccc ctccaaca                            1898
```